United States Patent
Palecek et al.

(10) Patent No.: US 9,453,201 B2
(45) Date of Patent: *Sep. 27, 2016

(54) GENERATION OF CARDIOMYOCYTES FROM HUMAN PLURIPOTENT STEM CELLS

(71) Applicant: Wisconsin Alumni Research Foundation, Madison, WI (US)

(72) Inventors: Sean Palecek, Verona, WI (US); Timothy Kamp, Madison, WI (US); Xiaojun Lian, Allston, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/592,678

(22) Filed: Jan. 8, 2015

(65) Prior Publication Data
US 2015/0152389 A1    Jun. 4, 2015

Related U.S. Application Data

(63) Continuation of application No. 13/650,687, filed on Oct. 12, 2012, now Pat. No. 8,951,798.

(60) Provisional application No. 61/546,686, filed on Oct. 13, 2011.

(51) Int. Cl.
*C12N 5/077* (2010.01)

(52) U.S. Cl.
CPC ....... *C12N 5/0657* (2013.01); *C12N 2501/155* (2013.01); *C12N 2501/16* (2013.01); *C12N 2501/415* (2013.01); *C12N 2501/727* (2013.01); *C12N 2501/998* (2013.01); *C12N 2501/999* (2013.01); *C12N 2506/02* (2013.01); *C12N 2506/45* (2013.01)

(58) Field of Classification Search
CPC .................. C12N 2501/415; C12N 2501/727; C12N 201/998; C12N 2501/999; C12N 2506/02; C12N 2506/45; C12N 5/0657; C12N 2501/155; C12N 2501/16
See application file for complete search history.

(56) References Cited

U.S. PATENT DOCUMENTS 8,951,798 B2 * 2/2015 Palecek ................ C12N 5/0657
435/366

FOREIGN PATENT DOCUMENTS

WO   WO 2008060446 A2 *  5/2008  ........... C12N 5/0657
WO       2008094597 A2     8/2008

OTHER PUBLICATIONS ten Berge et al., Cell Stem Cell, (3): 508-518, 2008.*
Anton et al, "β-Catenin signaling contributes to stemness and regulates early differentiation in murine embryonic stem cells", FEBS Lett., 2007, vol. 581, No. 27, pp. 5247-5254.
Baba et al., "Constitutively Active β-Catenin Confers Multilineage Differentiation Potential on Lymphoid and Myeloid Progenitors", Immunity, 2005, vol. 23, No. 6, pp. 599-609.
Chen et al., "Small molecule-mediated disruption of Wnt-dependent signaling in tissue regeneration and cancer", Nat. Chem. Biol., 2009, vol. 5, No. 2, pp. 100-107.
Franco et al., "Myosin light chain 2a and 2v identifies the embryonic outflow tract myocardium in the developing rodent heart", Anat. Rec., 1999, vol. 254, pp. 135-146.
Gurney et al., "Wnt pathway inhibition via the targeting of Frizzled receptors results in decreased growth and tumorigenicity of human tumors", Proc. Natl. Acad. Sci. USA, 2012, vol. 109, No. 29, pp. 11717-11722.
Hagen et al., "Expression and Characterization of GSK-3 Mutants and Their Effect on β-Catenin Phosphorylation in Intact Cells", J. Biol. Chem., 2002, vol. 26, pp. 23330-23335.
Hao et al., "In Vivo Structure-Activity Relationship Study of Dorsomorphin Analogues Identifies Selective VEGF and BMP Inhibitors", A.C.S. Chem. Biol., 2010, vol. 5, No. 2, pp. 245-253.
He et al., "A Monoclonal Antibody against Wnt-1 Induces Apoptosis in Human Cancer Cells", Neoplasia, 2004, vol. 6, No. 1, pp. 7-14.
Ieda et al., "Direct Reprogramming of Fibroblasts into Functional Cardiomyocytes by Defined Factors", Cell, 2010, vol. 142, No. 3, pp. 375-386.
Inman et al., "SB-431542 Is a Potent and Specific Inhibitor of Transforming Growth Factor-β Superfamily Type I Activin Receptor-Like Kinase (ALK) Receptors ALK4, ALK5, and ALK7", Mol. Pharmacol., 2002, vol. 62, No. 1, pp. 65-74.
Kubalak et al., "Chamber specification of atrial myosin light chain-2 expression precedes septation during murine cardiogenesis", J. Biol. Chem., 1994, vol. 269, pp. 16961-16970.
Matsui et al., "Induction of Initial Cardiomyocyte_-Actin-Smooth Muscle-Actin—in Cultured Avian Pregastrula Epiblast: A Role for Nodal and BMP Antagonist", Dev. Dynam., 2005, vol. 233, No. 4, pp. 1419-1429.
Nakajima et al., "Significance of Bone Morphogenetic Protein-4 Function in the Initial Myofibrillogenesis of Chick Cardiogenesis", Develop. Biol., 2002, vol. 245, No. 2, pp. 291-303.
Ren et al., "Small molecule Wnt inhibitors enhance the efficiency of BMP-4-directed cardiac differentiation of human pluripotent stem cells", J. Mol. Cell. Cardiol., 2011, vol. 51, No. 3, pp. 280-287.
Ruzicka and Schwartz, "Sequential activation of alpha-actin genes during avian cardiogenesis: vascular smooth muscle alpha-actin gene transcripts mark the onset of cardiomyocyte differentiation", J. Cell Biol., 1988, vol. 107, pp. 2575-2586.

(Continued)

*Primary Examiner* — Thaian N Ton
(74) *Attorney, Agent, or Firm* — Quarles & Brady LLP

(57) ABSTRACT

Methods for generating high-yield, high-purity cardiomyocyte progenitors or cardiomyocytes from pluripotent cells are described. Wnt/β-catenin signaling is first activated in pluripotent cells, e.g., by inhibition of Gsk-3 to obtain a first population of cells. Wnt/β-catenin signaling is then inhibited in the first cell population to induce cardiogenesis under fully defined, growth factor free culture conditions.

21 Claims, 27 Drawing Sheets

(56) References Cited

OTHER PUBLICATIONS

Segev et al., "Molecular analysis of cardiomyocytes derived from human embryonic stem cells", Dev. Growth Differ., 2005, vol. 47, pp. 295-306.
Sugi and Lough, "Onset of Expression and Regional Deposition of Alpha-Smooth and Sarcomeric Actin During Avian Heart Development", Dev. Dyn., 1992, vol. 193, pp. 116-124.
Tran et al., "Wnt3a-Induced Mesoderm Formation and Cardiomyogenesis in Human Embryonic Stem Cells", Stem Cells, 2009, vol. 27, No. 8, pp. 1869-1878.
Wang et al, "Cardiac Induction of Embryonic Stem Cells by a Small Molecule Inhibitor of Wnt/β-Catenin Signaling", A.C.S. Chem. Biol., 2011, vol. 6, No. 2, pp. 192-107.
Willems et al., "Small-Molecule Inhibitors of the Wnt Pathway Potently Promote Cardiomyocytes From Human Embryonic Stem Cell-Derived Mesoderm", Circ. Res., 2011, vol. 109, No. 4, pp. 360-364.
Lian, X. et al., Robust cardiomyocyte differentiation from human pluripotent stem cells via temporal modulation of canonical Wnt signaling, Proc. Natl. Acad. Sci., 2012, ovl. 109, No. 27, pp. E1848-E1857.
Lian, X. et al., "Directed cardiomyocyte differentiation from human pluripotent stem cells by modulating Wnt/[beta]-catenin signaling under fully defined conditions", Nature Protocols, 2012, vol. 8, No. 1, pp. 162-175.
Gonzalez, et al. Stepwise Chemically Induced Cardiomyocyte Specification of Human Embryonic Stem Cells, Angew. Chem. Int. Ed. 2011, 50, 11181-11185.
Graichen, et al. Enhanced cardiomyogenesis of human embryonic stem cells by a small molecular inhibitor of p38 MAPK. Differentiation 2008, 76:357-370.
Zhang, et al. Direct differentiation of atrial and ventricular myocytes from human embryonic stem cells by alternating retinoid signals, Cell Research (2011) 21:579-587.
Davidson, et al. Wnt/β-catenin signaling promotes differentiation, not self-renewal, of human embryonic stem cells and is repressed by Oct4, PNAS, Mar. 20, 2012, vol. 109, No. 12, 4485-4490.

Nakanishi, et al. Directed induction of anterior and posterior primitive streak by Wnt from embryonic stem cells cultured in a chemically defined serum-free medium, The FASEB Journal, Research Communication, Jan. 2009, vol. 23, 114-122.
Qyang, et al. The Renewal and Differentiation of Isl1+ Cardiovascular Progenitors Are Controlled by a Wnt/β-Catenin Pathway, Cell Stem Cell, Aug. 2007, 1, 165-179.
Shiraki et al, Differentiation of mouse and human embryonic stem cells into hepatic lineagesGenes to Cells, 13:731-746,2008.
Puceat, Protocols for cardiac differentiation of embryonic stem cells, Methods, 45: 168-171, 2008.
Wobus et al., Retinoic Acid Accelerates Embryonic Stem Cell-Derived Cardiac Differentiation and Enhances Development of Ventricular Cardiomyocytes. (1997) J Mol Cell Cardiology 29:1525.
Xu et al., Characterization and Enrichment of Cardiomyocytes Derived From Human Embryonic Stem Cells, (2002) Circulation Research 91 :50.
Wobus et al., Specific effects of nerve growth factor on the differentiation pattern of mouse embryonic stem cells in vitro, (1988) Biomed. Biochim Acta 12:965.
Schuldiner, Effects of eight growth factors on the differentiation of cells derived from human embryonic stem cells, (2000) PNAS 97:11307.
Kramer et al., Embryonic stem cell-derived chondrogenic differentiation in vitro: activation by BMP-2 and BMP-4, (2000) Mech. of Dev. 92:193.
Johansson et al. Evidence for Involvement of Activin A and Bone Morphogenetic Protein 4 in Mammalian Mesoderm and Hematopoietic Development, (1995) Mol and Cell Biol. 15:141.
Paige et al., Endogenous Wnt/P-Catenin Signaling Is Required for Cardiac Differentiation in Human Embryonic Stem Cells, PloS One, E11134; 5(6): 1-8, Jun. 2010.
Thomson et al., Embryonic Stem Cell Lines Derived from Human Blastocysts, Science 282, 1145-7 (1998).
Zhang et al., Functional Cardiomyocytes Derived From Human Induced Pluripotent Stem Cells, Circ Res. 2009;104: e30-e41.

\* cited by examiner

FIG. 7C-G
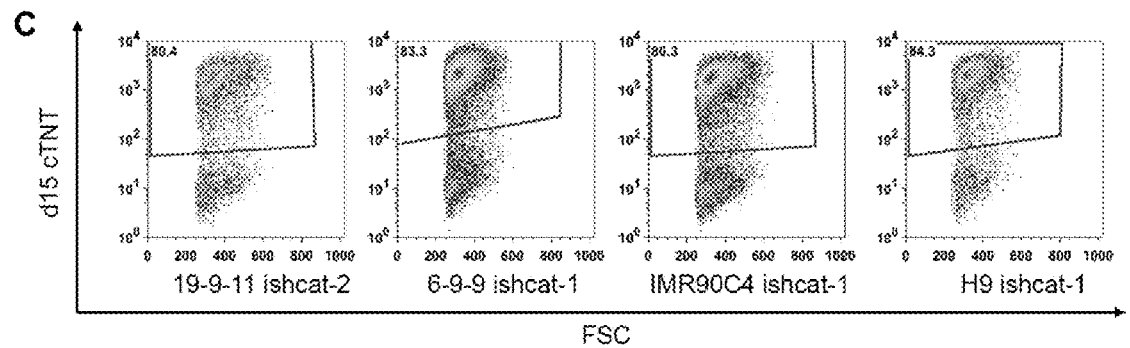
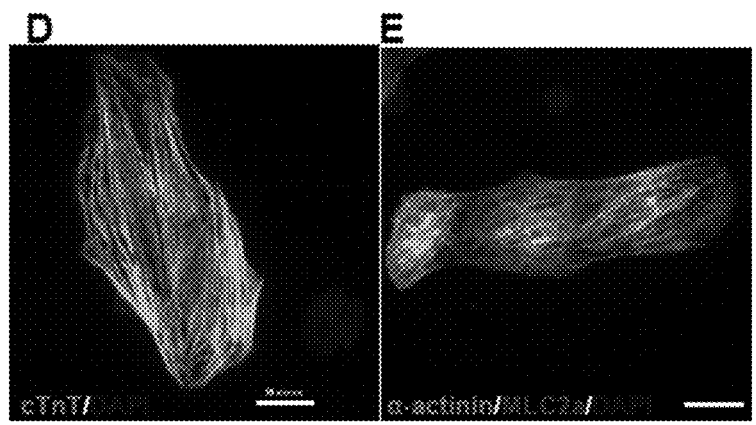
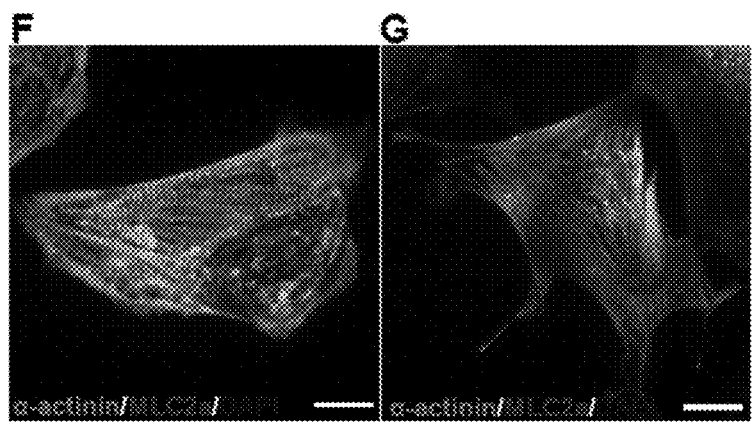

GENERATION OF CARDIOMYOCYTES FROM HUMAN PLURIPOTENT STEM CELLS

CROSS-REFERENCE TO RELATED APPLICATIONS

This patent application is a continuation of U.S. patent application Ser. No. 13/650,687, filed Oct. 12, 2012, now allowed, which claims priority to U.S. provisional patent application No. 61/546,686, filed on Oct. 13, 2011, each of which is incorporated by reference in its entirety as if fully set forth herein.

STATEMENT REGARDING FEDERALLY SPONSORED RESEARCH OR DEVELOPMENT

This invention was made with government support under EB007534 awarded by the National Institutes of Health and 0735903 awarded by the National Science Foundation. The government has certain rights in the invention.

BACKGROUND

Generating cardiovascular cells from pluripotent stem cells holds great promise for cardiovascular research and therapy. However, cardiogenesis is regulated by numerous developmental pathways. Moreover, differentiation of pluripotent stem cell into cardiac cells is inefficient and results in heterogeneous cultures, limiting the usefulness of this approach. Pluripotent stem cells, such as human embryonic stem (hES) cells and induced pluripotent stem (iPS) cells, collectively human pluripotent (hPS) cells can perpetually proliferate and differentiate into derivatives of all three embryonic germ layers (Thomson et al., Science 282:1145 (1998); Odorico et al., Stem Cells 19:193 (2001); Yu et al., Science 318(5858):1917 (2007)). Pluripotent stem cell cultures can differentiate spontaneously, yielding a seemingly random variety of cells (Watt and Hogan, Science 287:1427 (2000)). The earliest pluripotent stem cell differentiation methods allowed stem cell aggregates to spontaneously differentiate and form embryoid bodies (EBs) which contain precursors of the three primary germ layers, including, in some cases, cardiomyocytes. Such methods are inefficient, however, as only few percent of the developing cells become cardiomyocytes.

More recent methods direct differentiation of ES and iPS cells (pluripotent cells generated by reprogramming somatic cells or differentiated progenitor cells to pluripotency) into cardiomyocytes without EB formation by sequentially applying various combinations of soluble, exogenous growth factors and small molecules to mimic cardiac development. Soluble factors important for embryonic cardiac development include Activin A, BMP4, nodal, Wnt agonists and antagonists, bFGF and other molecules (Conlon et al., Development 120(7):1919 (1994); Lough et al., Dev. Biol. 178(1):198 (1996); Mima et al., PNAS 92(2):467 (1995); Zaffran and Frasch, Circ. Res. 91 (6), 457 (2002)). The addition of FGF2, Activin A, BMP4, DKK1 and VEGF, can enhance cardiomyocyte differentiation in embryoid bodies (EBs) (Yang et al., Nature 453:524-528 (2008)). However, this protocol is labor-intensive and not applicable to all pluripotent cell lines since it requires monitoring of KDR/c-kit (Yang et al., Nature 453:524-528 (2008)) or Flk1/PDGFRα (Kattman et al., Cell Stem Cel/8:228-240 (2011)) expression and optimization of growth factor concentrations for efficient cardiac development in various hPSC lines. Protocols for cardiomyocyte progenitor and cardiomyocyte differentiation that do not require cell line-specific optimization are desirable. Identification of defined factors that promote cardiomyocyte progenitor and cardiomyocyte differentiation has enabled development of monolayer-based directed differentiation protocols, such as, sequential treatment of Activin A and BMP4, which has been reported to generate greater than 30% cardiomyocytes in the H7 hESC line (Laflamme et al., Nat. Biotechnol. 25:1015-1024 (2007)). However, the efficiency of the Activin A and BMP4 directed differentiation protocol can be highly variable between cell lines and experimental repeats (Paige et al., PLoS One 5: e11134 (2010)).

Apart from their somatic cell origin, iPS cells share many characteristics of embryonic stem cells, such as the ability to grow perpetually and to differentiate into cells of all three germ layers. Like ES cells, iPS cells express pluripotency markers, such as OCT-4, SSEA-3, SSEA-4, TRA-1-60, TRA-1-81, and Nanog. iPS cells have been generated using retroviral vectors that randomly insert exogenous DNA into the target cell genome. Vector- and transgene-free iPS cells have been generated by using non-integrating vectors. Using non-integrating vectors avoids the risk of aberrant cellular gene expression and neoplastic growth (Okita et al. Nature 448:313 (2007)). Loss of the reprogramming vector also avoids perpetual expression of transgenes that can induce programmed cell death (apoptosis) (Askew et al., Oncogene 6:1915 (1991), Evan et al., Cell 69:119 (1992)) and interfere with subsequent differentiation of iPS cells.

More recently, methods were devised for reprogramming somatic cells using oriP/Epstein-Barr nuclear antigen-1 (EBNA1)-based episomal vectors that do not integrate into the genome and are lost from the cells after reprogramming (Yu et al., Science 324(5928):797 (2009)). iPS cells generated by this method are vector- and transgene-free and, as such, are well suited for clinical application. However, vector-free iPS cells have not yet been demonstrated to differentiate into clinically-applicable cardiomyocyte progenitors and cardiomyocytes with high efficiency (e.g., >90%) under fully defined conditions (both medium and substrate are defined).

Wnt proteins control morphogenesis, and are involved in development, stem cell differentiation control, and cell malignant transformation. The Wnt signaling pathway is a key regulator of cardiogenesis in vivo and in vitro. In chick and frog embryos, canonical Wnt signaling represses early cardiac specification (Marvin et al., Genes Dev. 15, 316-327 (2001); Schneider and Mercola, Genes Dev. 15, 304-315 (2001); Tzahor and Lassar, Genes Dev 15, 255-260 (2001)) and has a biphasic effect in zebrafish, mouse embryos, and mouse embryonic stem cells (Naito et al., Proc. Natl Acad. Sci. U.S.A. 103, 19812-19817 (2006); Ueno et al., Proc. Natl. Acad. Sci. U.S.A. 104, 9685-9690 (2007), with early Wnt signaling enhancing cardiogenesis and later signaling repressing heart development. Endogenous Wnt signaling is also required after treatment to differentiate hES cells to cardiomyocytes with Activin A and BMP4 (Paige et al., PLoS One 5: e11134 (2010)). However, it remains unknown whether differentiation of human pluripotent stem cells to cardiomyoctes conserves such stage-specific Wnt signaling roles.

The canonical Wnt pathway describes a series of events that occur when Wnt ligands bind to cell-surface receptors of the Frizzled family, causing the receptors to activate Dishevelled family proteins, resulting in a change in the amount of β-catenin that reaches the nucleus. Modulation of Gsk3 and Wnt pathway signaling triggers expression of a variety of developmental cues (e.g. Nodal (Kattman et al., Cell Stem Cell, 8:228-240 (2011)), BMP2/4 (Kattman et al., 2011; Laflamme et al., Nat. Biotech 25:1015-1024 (2007)), Noggin (Ma et al., Cell Res. 21:579-587 (2011)), WNT3a (Tran et al., Stem Cells, 27:1869-1878 (2009)) and WNT8a (Paige et al., PLoS One 5:e11134 (2010)) and transcription factors involved in cardiomyocyte differentiation (e.g. T (Asashima et al., Faseb J. 23:114-122(2009)) and MIXL1 (Davis et al., Blood 111:1876-1884 (2008)), ISL1 (Bu et al., Nature 460:113-117 (2009) and NKX2-5 (Lints et al., Development 119:969 (1993)), TBX5 (Bruneau et al., Dev Biol 211:100-108 (1999)), GATA4 (Kuo et al., Gene Dev 11:1048-1060 (1997a); Kuo et al., Circulation 96:1686-1686 (1997), and MEF2C (Edmondson et al., Development 120: 1251-1263 (1994)). There is in the art a need for a cardiac differentiation protocol that uses completely defined, growth factor-free culture conditions to produce cardiomyocyte progenitors and cardiomyocytes from hPS cells.

BRIEF SUMMARY

The invention relates generally to methods for cardiac induction in hPS cells and, more particularly, to methods for generating, from hPS cells, populations of cardiomyocyte progenitors, which go on to become functional cardiomyocytes under chemically-defined, growth factor-free conditions by sequential activation and inhibition of Wnt/β-catenin signaling.

Accordingly, in one aspect provided herein is a method for generating a population of cardiomyocyte progenitors from pluripotent stem cells, comprising: (i) activating Wnt/β-catenin signaling in cultured pluripotent stem cells (e.g., primate pluripotent stem cells, human pluripotent stem cells, or non-human primate pluripotent stem cells) to obtain a first cell population; (ii) culturing the first cell population for a period following the end of the activating step; and (iii) inhibiting Wnt/β-catenin signaling in the cultured first cell population after the culturing period in step (ii) to obtain a second cell population comprising cardiomyocyte progenitors.

In some embodiments of the just-mentioned method, activating the Wnt/β-catenin signaling comprises inhibiting Gsk3 in the pluripotent stem cells. In some embodiments, Gsk3 in the pluripotent stem cells is inhibited by contacting the pluripotent stem cells with a small molecule that inhibits Gsk3. In some embodiments, the small molecule inhibitor that inhibits Gsk3 is CHIR 99021, CHIR 98014, BIO-acetoxime, BIO, LiCl, SB 216763, SB 415286, AR A014418, 1-Azakenpaullone, and Bis-7-indolylmaleimide, or a combination thereof. In another embodiment, the small molecule Gsk3 inhibitor to be used is CHIR 99021, CHIR 98014, and BIO-acetoxime. In one embodiment, the small molecule Gsk3 inhibitor to be used is CHIR 99021.

In some embodiments, inhibiting Gsk3 in the pluripotent stem cells includes RNA interference knockdown of Gsk3. In other embodiments, inhibiting Gsk3 in the pluripotent stem cells includes overexpression of a dominant negative form of Gsk3.

In yet other embodiments, the Wnt/β-catenin pathway signaling is activated in the cultured pluripotent stem cells by overexpressing β-catenin in the cultured pluripotent stem cells.

In some embodiments of the above-mentioned method, inhibiting Wnt/β-catenin signaling in the first cell population includes contacting the first cell population with a small molecule that inhibits Wnt/β catenin signaling. In some embodiments, the small molecule that inhibits Wnt/β catenin signaling is a small molecule that stabilizes axin and stimulates β-catenin degradation. In one embodiment, the small molecule that stabilizes axin and stimulates β-catenin degradation includes 3,5,7,8-Tetrahydro-2-[4-(trifluoromethyl)phenyl]-4H-thiopyrano[4,3-d]pyrimidin-4-one ("XAV939").

In other embodiments, the small molecule that inhibits Wnt/β catenin signaling is a small molecule that prevents palmitylation of Wnt proteins by porcupine. In some embodiments, the small molecule that prevents palmitylation of Wnt proteins by porcupine includes N-(6-Methyl-2-benzothiazolyl)-2-[(3,4,6,7-tetrahydro-4-oxo-3-phenylthieno[3,2-d]pyrimidin-2-yl)thio]-acetamide ("IWP2"), 2-(3,4,6,7-tetrahydro-3-(2-methoxyphenyl)-4-oxothieno[3,2-d] pyrimidin-2-ylthio)-N-(6-methylbenzo[d]thiazol-2-yl) acetamide ("IWP4"), or a combination thereof.

In yet another embodiment, the small molecule that inhibits Wnt/β catenin signaling is a small molecule that increases the activity level of casein kinase 1α. In some embodiments, the small molecule that increases the activity level of casein kinase 1α is 6-(Dimethylamino)-2-[2-(2,5-dimethyl-1-phenyl-1H-pyrrol-3-yl)ethenyl]-1-methyl-4,4'-methylenebis[3-hydroxy-2-naphthalenecarboxylate](2:1)-quinolinium, or a combination thereof.

In further embodiments, inhibiting the Wnt/β-catenin signaling in the first cell population includes contacting the first cell population with at least one antibody that blocks activation of a Wnt ligand receptor. In some embodiments, the at least one antibody binds to one or more Wnt ligand family members. In other embodiments, the at least one antibody binds to the Wnt ligand receptor.

In other embodiments, inhibiting the Wnt/β-catenin signaling in the first cell population comprises reducing β-catenin expression in the first cell population. In some embodiments, reducing β-catenin expression comprises expressing shRNA for β-catenin in the first cell population. In some embodiments, reducing β-catenin expression comprises overexpressing Axin2 in the first cell population.

In further embodiments of the above-mentioned method, the pluripotent stem cells in step (i), the first cell population in step (ii), or the second population in step (iii) are cultured under exogenous growth factor-free conditions.

In some embodiments, the second cell population is cultured for a period after ending the inhibition of Wnt/β-catenin signaling initiated in step (iii) to obtain a cell population comprising cardiomyocytes.

In some embodiments, where a cell population comprising cardiomyocytes is obtained, at least 70% of the cells in the cell population are cardiac troponinT (cTnT)-positive, and the cell population comprising the at least 70% cTnT-positive cells is obtained without the use of a cell separation step on the second cell population.

In another aspect, provided herein is a method for culturing pluripotent stem cells to obtain a population of cardiomyocytes, the method comprising the steps of: sequentially inhibiting Gsk3 in the pluripotent cells and then inhibiting Wnt signaling in the Gsk3 inhibited cells; and culturing the sequentially inhibited cells in a culture medium to form a differentiated cell population comprising cardiomyocytes.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 1A depicts H9-7TGP cells treated with different concentrations of CHIR99021(CH) in mTeSR®1 for 4 days. FIG. 1B depicts immunofluorescent staining for Oct4, Isl1, and Nkx2.5 relative to GFP expression in H9-7TGP cells treated with 12 μM CHIR99021 in mTeSR1 for 4 days. Scale bar=50 μm. FIG. 1C depicts H9 cells cultured on MEFs treated with CHIR99021 in hESC medium for 3 days before forming EBs. FIG. 1D depicts percentage of cTnT+ cells in day 15 culture assessed by flow cytometry. H9 cells were cultured on Matrigel® and treated with DMSO, 1 μM CHIR99021, or 1 μM BIO for 3 days before exposure to 100 ng/ml Activin A at day 0 and 5 ng/ml BMP4 at day 1 in RPMI/B27-insulin medium. # p<0.005, CH versus DMSO, BIO versus DMSO; t test.

FIG. 2A schematically depicts a 7TGP lentiviral promoter-reporter construct, wherein 'TCF BS' represents 7 repeats of TCF/LEF consensus promoter binding sites. FIG. 2B depicts GFP expression detected by immunofluorescent microscopy of H9 7TGP cells cultured in UM on MEF feeders, or in CM, mTeSR1, or mTeSR1+12 μM CH on Matrigel® for 3 days following seeding. Scale bar=50 FIG. 2C depicts GFP expression in H1 7TGP cells cultured in mTeSR1+15 μM CH on Matrigel® at different time points after CH addition. FIG. 2D depicts GFP localization and immunostaining of Oct4 and Isl1 in 19-9-11 7TGP cells cultured in mTeSR1+12 μM CH on Matrigel® for 3 days. Scale bar=50 μm. FIG. 2E depicts cTnT expression 15 days after initiation of differentiation in IMR90C4 cells cultured in mTeSR1 containing different concentrations of BIO. Differentiation was induced by 100 ng/ml Activin A at day 0 and 5 ng/ml BMP4 at day 1 in RPMI/B27-insulin medium. #p<0.005, each point versus no BIO; t test.

FIG. 3A schematically depicts a construct for constitutive knockdown of β-catenin expression and shRNA sequences targeting β-catenin. FIG. 3B depicts quantitative RT-PCR gene expression analysis of β-catenin and β-actin for scramble and β-catenin knockdown lines in 19-9-11 and H9 cells. # p<0.005, shcat-1 versus scramble, shcat-2 versus scramble; t test. FIG. 3C depicts RT-PCR analysis of pluripotent, mesendoderm, early mesoderm, and early cardiac gene expression of same cells. 19-9-11 shcat-2 and scramble cells were cultured on Matrigel® with mTeSR1 containing 12 μM CH for 4 days. FIG. 3D depicts Oct4 expression measured by flow cytometry of 19-9-11 shcat-2 and scramble lines cultured on Matrigel® with mTeSR1 containing 12 μM CH for 4 days. Each line represents an independent replicate.

FIG. 4A depicts β-catenin expression, measured by RT-PCR, in H9 β-catenin knockdown and scramble cell lines cultured in mTeSR1. FIG. 4B depicts β-catenin expression measured by qRT-PCR in H7 shcat-2 and scramble lines. Error bars represent the s.e.m. of three samples. #p<0.005, shcat-2 versus scramble; t test. FIG. 4C depicts immunostaining of Oct4 in H9 scramble, shcat-1, shcat-2 cells cultured in mTeSR1 on Matrigel® for 3 days. Scale bar=50 μm. FIG. 4D depicts Oct4 expression, measured by flow cytometry, in 19-9-11 shcat-2 and scramble lines cultured in mTeSR1 on Matrigel® for 3 days. The blue (scramble) and green (shcat-2) histogram represents Oct4 expression and the red histogram is an isotype control. FIG. 4E depicts cell morphology, which was assessed by phase contrast imaging of 19-9-11 shcat-2 and scramble cells cultured on Matrigel® in mTeSR1 containing 12 μM CH for 4 days. Scale bar=50 μm. FIG. 4F depicts 19-9-11 iscramble cells and FIG. 4G depicts 19-9-11 ishcat-2 cells, each cultured in mTeSR1 for 5 days then exposed to 100 ng/ml Activin A at day 0 and 5 ng/ml BMP4 at day 1, with 2 μg/ml doxycycline (dox) addition at the indicated times. 15 days after initiation of differentiation, cells were counted and analyzed for cTnT expression by flow cytometry. Error bars represent the s.e.m. of three independent experiments. #p<0.005, each time point versus no dox; t test.

FIG. 5A schematically depicts an inducible shRNA construct for 0-catenin knockdown and shRNA sequences targeting β-catenin. FIG. 5B depicts representative phase contrast and mCherry epifluorescence images of 19-9-11 cells transduced with lentvirial vectors containing the constructs described in FIG. 5A and selected by puromyocin treatment. FIG. 5C depicts β-catenin expression, measured by qPCR, in 19-9-11 ishcat-1 and ishcat-2 cells cultured in mTeSR1 containing 2 μg/ml dox for 3 days. Error bars represent the s.e.m. of 3 samples. # p<0.005, ishcat-1 versus iscramble, ishcat-2 versus iscramble; t test. FIG. 5D depicts cTnT expression 15 days after initiation of differentiation in 19-9-11 ishcat-1 cells cultured in mTeSR1 for 5 days then exposed to 100 ng/ml Activin A at day 0 and 5 ng/ml BMP4 at day 1, with 2 μg/ml dox addition at the indicated times. Error bars represent the s.e.m. of three independent experiments. # p<0.005, each time point versus no dox; t test.

FIG. 6A schematically depicts a protocol for defined, growth factor free differentiation of hPS cells expressing dox-inducible β-catenin shRNA to cardiomyocytes via treatment with small molecules. FIG. 6B depicts 19-9-11 ishcat-2 cells cultured as indicated in FIG. 6A, with dox added at different time points following 12 μM CH treatment. At day 15 cells were analyzed for cTnT expression by flow cytometry. Error bars represent the s.e.m. of three independent experiments. *p<0.05; # p<0.005, each time point versus no dox; t test. FIG. 6C depicts cardiomyocytes generated from 19-9-11 ishcat-1 cells using the protocol described in FIG. 6A, with 12 μM CH treatment at day 0 and 2 μg/ml dox treatment 36 hr later. At day 30, cells were individualized and replated on 0.1% gelatin coated coverslips. Immunostaining for α-actinin and MLC2a shows sarcomere organization. Scale bar=50 μm. FIG. 6D depicts transmission electron microscopic images of beating clusters derived from 19-9-11 ishcat-1 line as described in FIG. 6C. Myofibrils (red arrowhead) with Z-bands (green arrowhead) and mitochondria (blue arrowhead) are shown. Scale bar=2 μm. FIG. 6E depicts microelectrode recordings of action potential activity collected at day 29 in cardiomyocytes derived from the 19-9-11 ishcat-1 cells differentiated as described in FIG. 6C. Dashed lines indicate 0 mV. FIG. 6F depicts representative recordings of APs collected during field stimulation at 1, 2, and 3 Hz as indicated (top). FIG. 6F also depicts bar graphs showing average (±s.e.m.) fractional changes in action potential duration at 90 and 50 percent repolarization obtained by normalizing to the values observed in response to 1 Hz stimulation (bottom). Data represent s.e.m. of 4 independent experiments.

FIGS. 7A-I illustrate cardiomyocyte content of differentiated cell population. FIG. 7A depicts results of flow cytometry of cTnT performed at day 15 post-addition of CH. 19-9-11 ishcat-1 cells were treated with different concentrations of CH in RPMI/B27-insulin for 24 hr and then the medium was changed to RPMI/B27-insulin at day 1. Starting from day 7, cells were cultured in RPMI/B27. Error bars represent the S.E.M. of three independent experiments. *p<0.05; #p<0.005, each point versus no CH; t test. FIG. 7B depicts cell counts and results of flow cytometry of cTnT performed at day 15 post-addition of CH. 19-9-11 ishcat-1 cells were cultured in mTeSR1 before exposure to 12 μM CH in RPMI/B27-insulin for 24 hr. 2 μg/ml dox was added at different time points following CH addition. Error bars represent the S.E.M. of three independent experiments. FIG. 7C depicts results of flow cytometry of cTnT expression cells performed 15 days following CH addition. 19-9-11 ishcat-2 and three additional hPS cell lines (IMR90C4, 6-9-9, and H9) transduced with inducible β-catenin shRNA construct ishcat-1 cells were cultured in mTeSR1 and treated with 12 μM CH followed by 2 μg/ml dox addition 36 hr later. FIG. 7D-G depict immunostaining of day 30 cardiomyocytes generated from (7D) 19-9-11 ishcat-1, (7E) IMR90C4 ishcat-1, (7F) 6-9-9 ishcat-1, and (7G) H9 ishcat-1 cells, each cultured in mTeSR1, and treated with 12 μM CH and 2 μg/ml dox addition 36 hr later. Cells were immunostained for cTnT, α-actinin, and MLC2a to show sarcomere structure. Scale bar=20 μm. FIG. 7H-I depict transmission electron microscopy images of beating clusters derived from 19-9-11 ishcat-1 cells following culture in mTeSR1 and treatment with 12 μM CH and 2 μg/ml dox addition at 36 hr later. Myofibrils (red arrowhead) with Z-bands (green arrowhead) and intercalated disks with desmosomes (pink arrowhead) are shown. Scale bar=200 nm.

FIG. 8A depicts pluripotent, mesendoderm, mesoderm, and cardiac gene expression in 19-9-11 ishcat-1 cells differentiated as described in FIG. 6A. At different time points, mRNA was collected and RT-PCR analysis was performed. FIG. 8B-D depict cTNT, MLC2v, MLC2a, and SMA expression, MF20 staining, Ki67 staining, and BrdU incorporation in 19-9-11 ishcat-1 cells differentiated as shown in FIG. 6C, with 12 μM CH added at day 0 and 2 μg/ml doxycline added 36 hr later. Error bars represent the s.e.m. of three independent experiments. Day 20, day 40 and day 60 are significantly different from each other (p<0.05) when data were compared using 1-way ANOVA and Tukey post tests.

FIG. 9A depicts the percentage of cTnT+ cells at day 15 in 19-9-11 ishcat-2 cells treated with 12 μM CH, 12 μM CH and 0.5-4 μM SB431542, or 12 μM CH and 0.2-1 μM DMH1 for 24 hr, wherein all samples were treated with 2 μg/ml dox 48 hr later. Error bars represent the s.e.m. of three independent experiments. *p<0.05; # p<0.005, each point versus control; t test. FIG. 9B depicts expression of BMP2/4 and expression and phosphorylation of SMAD proteins in 19-9-11 ishcat-2 cells undergoing differentiation by 100 ng/ml Activin A at day 0 and 5 ng/ml BMP4 at day 1 or treatment with either 12 μM CH, 12 μM CH and 1 μM DMH1, or 12 μM CH and 1 μM SB431542 for 24 hr followed by 2 μg/ml dox addition at 36 hr. FIG. 9C depicts Wnt and TGFβ pathway genes expression assessed by RT-PCR in 19-9-11 ishcat-2 cells differentiated to cardiomyocytes as shown in 4A, with 12 μM CH treatment at day 0 and 2 μg/ml dox addition at 36 hr.

FIG. 10A depicts expression and phosphorylation of Smad proteins in 19-9-11 ishcat-1 cells cultured in mTeSR1 treated with 12 μM CH, 12 μM CH and 0.5-4 μM SB431542, or 12 μM CH and 0.2-1 μM DMH1 for 24 hr in RPMI/B27-insulin, at different time points following CH treatment. All samples were treated with 2 μg/ml dox 36 hr later. The plot shows densitometry measurements of pSmad1/5 protein bands relative to total Smad1 and pSmad2 protein bands relative to total Smad2. FIG. 10B depicts MF20 expression in day 15 19-9-11 cells cultured in mTeSR1 on Matrigel® and treated with 12 μM CH followed by 1 μM IWP4 addition 2 or 3 days later. Error bars represent the S.E.M. of three independent experiments. FIG. 10C depicts cTnT expression in day 15 19-9-11 cells cultured in mTeSR1 on Matrigel® for 5 days before exposure to indicated concentrations of CH98014, BIO-acetoxime, or BIO at day 0 for 24 hr and IWP4 added at day 3, in RPMI/B27-insulin.

FIG. 11A depicts cTnT MF20 expression in day 15 19-9-11 cells cultured on Matrigel® in mTeSR1 for 5 days before exposure to 12 μM CH at day 0 and 0-7 μM IWP4 or 5 IWP2 at day 3 in RPMI/B27-insulin. Error bars represent s.e.m. of 3 independent experiments. # p<0.005, each point versus no drug; t test. FIG. 11B depicts cTnT MF20 expression in day 15 IMR90C4 and 19-9-11 cells cultured on Synthemax® plates in mTeSR1 for 5 days before exposure to 12 μM CH at day 0 and 5 μM IWP4 at day 3 in RPMI/B27-insulin. IMR90C4 cells were differentiated with 100 ng/ml Activin A at day 0 and 5 ng/ml BMP4 at day 1 as a control. Error bars represent s.e.m. of 3 independent experiments.

Figure 1A:
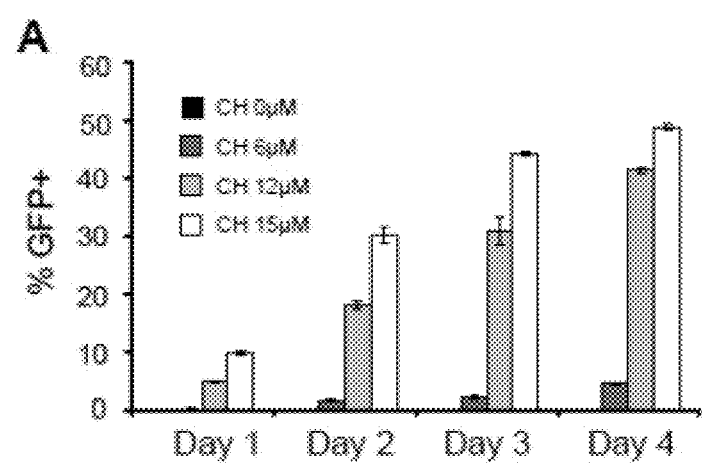
FIGS. 1A-D illustrate that treatment of hPS cells with Gsk3 inhibitors enhances cardiac differentiation.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, preferred methods and materials are described herein.

In describing the embodiments and claiming the invention, the following terminology will be used in accordance with the definitions set out below.

As used herein, "about" means within 5% of a stated concentration range or within 5% of a stated time frame.

The terms "defined culture medium," "defined medium," and the like, as used herein, indicate that the identity and quantity of each medium ingredient is known.

As used herein, the terms "chemically-defined culture conditions," "fully defined, growth factor free culture conditions," and "fully-defined conditions" indicate that the identity and quantity of each medium ingredient is known and the identity and quantity of supportive surface is known.

As used herein, "effective amount" means an amount of an agent sufficient to evoke a specified cellular effect according to the present invention.

As used herein, the term "Gsk 3 inhibited cells" refers to (i) cells in which Gsk3 has previously been inhibited, but in which Gsk3 is no longer actively inhibited; or (ii) cells in which Gsk3 is not being actively inhibited, but for which a parental stem cell or progenitor cell population had had Gsk3 inhibited. Within the context of the present disclosure such "Gsk 3 inhibited cells" correspond to some embodiments in which a first cell population (comprising mesendodermal markers) is obtained after exposing human pluripotent stem cells to a Gsk3 inhibitor for a defined period of time, after which Gsk-3 is no longer actively inhibited.

As used herein, the term "pluripotent cell" means a cell capable of differentiating into cells of all three germ layers. Examples of pluripotent cells include embryonic stem cells and induced pluripotent stem (iPS) cells. As used herein, "iPS cells" refer to cells that are substantially genetically identical to their respective differentiated somatic cell of origin and display characteristics similar to higher potency cells, such as ES cells, as described herein. The cells can be obtained by reprogramming non-pluripotent (e.g., multipotent or somatic) cells.

As used herein, "iPS cell derivation" means reprogramming a somatic cell to become pluripotent.

The present invention involves a method for differentiating hPS cells to obtain a population of cardiomyocyte progenitors, the method including the steps of: sequentially activating Wnt/β-catenin pathway signaling in pluripotent stem cells to obtain a first cell population characterized by a majority of cells expressing mesodermal or endodermal markers ("mesendoderm" markers). Subsequently, the first population of cells is cultured for a period without further activation of Wnt/β-catenin pathway signaling. Afterwards, Wnt/β-catenin pathway signaling in the first population of cells is inhibited for a period of time, and then relieved of Wnt/β-catenin pathway signaling to differentiate the first population of cells into a second cell population containing cardiomyocyte progenitors. In some embodiments, the second cell population, comprising cardiomyocyte progenitors, is then further cultured for a period of time to obtain a population of cells comprising cardiomyocytes.

The methods have valuable applications such as inexpensive and reproducible generation of human cardiomyocyte progenitors or cardiomyocytes. Generating cardiomyocyte progenitors or cardiomyocytes in completely chemically-defined conditions might facilitate translation of these cells to regenerative therapies.

As disclosed herein, in some embodiments of the differentiation methods, exogenous TGFβ superfamily growth factors are not required to generate cardiomyocyte progenitors or cardiomyocytes from pluripotent cells. While not wishing to be bound by theory, it is believed that, in various embodiments described herein, undifferentiated pluripotent stem cells or mesendoderm cells, including those differentiated from pluripotent stem cells, provide sufficient endogenous Nodal and BMP proteins. As shown herein, in some cases, substantially growth factor-free directed differentiation, including temporal modulation of Wnt pathway regulators as set forth herein, can generate up to 95% cTnT+ cardiomyocytes from pluripotent stem cells.

Another advantage is that in some embodiments of the disclosed methods, differentiation of hPS cells into a differentiated population of cells comprising cardiomyocyte progenitors or cardiomyocytes is carried out under chemically-defined conditions, whereas most, if not all, existing protocols require expression of transcription factors, integration of cardiac specific promoter driven selection cassettes, or application of serum and/or growth factors.

As described in further detail below, the inventors' simplified protocols target key regulatory elements of the Wnt/β-catenin signaling pathway, simplifying the steps and components involved in deriving cardiomyocyte progenitors and cardiomyocytes from pluripotent stem cells.

Timing

In some embodiments, in the first step, i.e., step (i) of the just-mentioned method, pluripotent stem cells to be differentiated are subjected to activation of Wnt/β-catenin pathway signaling for a period of about 8 hours to about 48 hours, e.g., about 8 hours, 12 hours, 16 hours, 20 hours, 24 hours, 28 hours, 32 hours, 36 hours, 40 hours, 44 hours, 48 hours, or another period of Wnt/β-catenin pathway signaling activation from about 8 hours to about 48 hours to obtain a first cell population of cells, characterized by the expression of mesendodermal markers. In one embodiment, pluripotent stem cells are subjected to Wnt/β-catenin pathway signaling activation for a period of about 24 hours.

In some embodiments, in step (ii) after the end of the Wnt/β-catenin pathway activation step, i.e., after the agent for activating the Wnt/β-catenin pathway signaling has been removed or has ended, the first population of cells is cultured in the absence of external Wnt/β-catenin pathway activation for a period of at least about 8 hours to about 60 hours, e.g., about 10 hours, 11 hours, 12 hours, 14 hours, 16 hours, 20 hours, 24 hours, 30 hours, 36 hours, 40 hours, 44 hours, 48 hours, 52 hours, 56 hours, 60 hours or another period from at least about 8 hours to about 60 hours. In one embodiment, this culture period is about 12 hours.

In one embodiment, this culture period is about 12 hours. In some embodiments, the culture period is about 48 hours.

In some embodiments, in step (iii), immediately after culture of the first population of cells in the absence of Wnt/β-catenin pathway activation, the first population is subjected to inhibition of Wnt/β-catenin pathway signaling. In some embodiments, step (iii) is initiated at least about 33 hours to about 74 hours following the beginning of step (i), e.g., at least about 34 hours, 36 hours, 38 hours, 39 hours, 40 hours, 45 hours, 50 hours, 60 hours, 65 hours, 68 hours, 69 hours, 70 hours, 72 hours, or another time point from at least about 33 hours to about 74 hours following the beginning of step (i). In some embodiments, step (iii) is initiated 36 hours after the beginning of step (i). In other embodiments, step (iii) begins 72 hours after the beginning of step (i).

In some embodiments, the medium from step (ii) is only partially replaced with fresh medium to obtain a "combined medium" in which the first cell population is cultured at the beginning of step (iii). In some embodiments, the proportion of fresh medium in the final culture medium volume at the beginning of step (iii) ranges from about 30% to about 70%, e.g., about 35%, 40%, 45%, 50%, 55%, 60%, 64% or another proportion from about 30% to about 70%. In some embodiments, the proportion of fresh medium in the final culture volume at the beginning of step (iii) is about 50%. In other embodiments, the medium from step (ii) is completely replaced with fresh medium at the beginning of step (iii).

In one embodiment, where β-catenin RNA interference is to be used to inhibit the Wnt/β-catenin signaling pathway, RNA interference is initiated about 36 hours following the beginning of Gsk3 inhibition. In another embodiment, where small molecule-mediated inhibition of the Wnt/β-catenin signaling pathway is to be used, the first cell population is contacted with the small molecule inhibitor at about 3 days following Gsk3 inhibition.

Typically, inhibition of Wnt/β-catenin signaling in the first population of cells during step (iii) is maintained for a period of at least about 1 day to about 6 days, e.g., about 1 day, 2 days, 2.5 days, 3 days, 3.5 days, 4 days, 5 days, or another period of Wnt/β-catenin signaling inhibition from at least about 1.5 days to about 6 days. In some embodiments, where a small molecule inhibitor is used to inhibit Wnt/β-catenin signaling, the first cell population is contacted with the small molecule for a period of about 2 days, and then culture of the first cell population continues in the substantial absence of the small molecule inhibitor. In other embodiments, where inducible RNA interference is used (e.g., with an inducing agent such as Doxycycline to drive expression of tet-on expression cassette) to knockdown expression of β-catenin, induction and maintenance of β-catenin is for a period of about 3.5 days, after which induction of β-catenin shRNA expression is terminated, and then culture of the first cell population continues in the substantial absence of the inducing agent.

While, in some cases, cells are cultured continuously from the beginning of step (i) to step (iii) to obtain a population comprising cardiomyocyte progenitors, in other cases cultured cells are removed from a culture substrate and frozen for storage thus allowing for the differentiation method to be resumed after thawing cells at a later date. For example, in some cases, the first population of cells obtained after step (i) is collected and stored frozen in any number of suitable cell cryopreservation media known in the art, and then later thawed and cultured to resume the differentiation method starting at step (ii) and continuing to step (iii) in which Wnt/β-catenin pathway signaling is inhibited to drive differentiation into a second cell population comprising cardiomyocytes.

In other embodiments, the second population of cells, comprising cardiomyocyte progenitors, is cryopreserved, and thawed at a later date for continued culture of the second population in order to obtain a population comprising cardiomyocytes. Accordingly, one of ordinary skill in the art will appreciate that, where the differentiation methods described herein include a cell freezing step, the absolute time interval between at least two steps will be different from the corresponding step interval in embodiments that do not include a freezing step.

Typically, the second cell population obtained by the disclosed methods comprises a very high proportion of cardiomyocyte progenitors. In some embodiments, the second cell population comprises about 50% to about 99% cardiomyocyte progenitors, e.g., about 52%, 55% 67%, 70%, 72%, 75%, 80%, 85%, 90%, 95%, 98%, or another percent of cardiomyocyte progenitors from about 50% to about 99% cardiomyocyte progenitors.

In some embodiments, after ending the inhibition of Wnt/β-catenin signaling initiated during step (iii), as described herein, the resulting second population of cells, comprising cardiomyocyte progenitors, is cultured for an additional period of time to obtain a cell population comprising cardiomyocytes. In some embodiments, the additional cell culture period for the second cell population ranges from at least about 20 days to about 200 days, e.g, about 23 days, 25 days, 27 days, 30 days, 35 days, 40 days, 45 days, 55 days, 70 days, 90 days, 100 days, 120 days, 150 days, 170 days, 180 days, 190 days, or another culture period, after ending inhibition of Wnt/β-catenin signaling, from at least about 20 days to about 200 days following the end of Wnt/β-catenin signaling inhibition. In one embodiment, the second population of cells is cultured for a period of at least about 25 days after ending inhibition of Wnt/β-catenin signaling.

In some embodiments, continued culture of the second population (in the absence of Wnt/β-catenin signaling inhibition) yields a cell population population comprising about 50% to about 99% cardiomyocytes, e.g., about 52%, 55% 67%, 70%, 72%, 75%, 80%, 85%, 90%, 95%, 98%, or another percent of cardiomyocytes from about 50% to about 99% cardiomyocytes.

In some embodiments, no cell separation step or method is used to obtain a second cell population comprising at least 70% cTnT-positive cells. In other embodiments, cell separation or enrichment methods, e.g., FACS, MACS, or laser-targeted ablation of non-cardiomyotcyes are used to obtain a second cell population further enriched in cardiomyocytes relative to the second cell population prior to application of a cell separation or enrichment method. Cardiomyocytes are identified by the presence of one or more cardiomyocyte markers (e.g., cTnT expression) or functional characteristics (e.g., spontaneous contractility).

Useful gene expression or protein markers for identifying cardiomyocyte progenitors or cardiomyocytes, include, but are not limited to, Smooth Muscle Actin, Cardiac Troponin T, light meromyosin MF20, sarcomeric myosin, Myosin Light Chain ventricular, Myosin Light Chain Atrial, and alpha-actinin, NKX2.5, TBX5, GATA4, MEF2, and combinations thereof. Such markers can be detected at the mRNA expression level or protein level by standard methods in the art.

In some embodiments, where cardiomyocytes are to be generated, certain cardiomyocyte functional criteria are also assessed. Such functional cardiomyocyte criteria include, but are not limited to, spontaneously contractility, response to electrical pacing, the presence of organized contractile structures, or a combination thereof.

Pluripotent stem cells (PSCs) suitable for the differentiation methods disclosed herein include, but are not limited to, human embryonic stem cells (hESCs), human induced pluripotent stem cells (hiPSCs), non-human primate embryonic stem cells (nhpESCs), non-human primate induced pluripotent stem cells (nhpiPSCs).

Activation of Wnt/β-Catenin Signaling

As will be appreciated by those of ordinary skill in the art, Wnt/β-catenin signaling can be activated by modulating the function of one or more proteins that participate in the Wnt/β-catenin signaling pathway to increase β-catenin expression levels or activity, TCF and LEF expression levels, or β-catenin/TCF/LEF induced transcriptional activity.

In some embodiments, activation of Wnt/β-catenin signaling is achieved by inhibition of Gsk3 phosphotransferase activity or Gsk3 binding interactions. While not wishing to be bound by theory, it is believed that inhibition of Gsk3 phosphorylation of β-catenin will inhibit tonic degradation of β-catenin and thereby increase β-catenin's level and activity to drive differentiation of pluripotent stem cells to an endodermal/mesodermal lineage. Gsk3 inhibition can be achieved in a variety of ways including, but not limited to, providing small molecules that inhibit Gsk3 phosphotransferase activity, RNA interference knockdown of Gsk3, and overexpression of dominant negative form of Gsk3. Dominant negative forms of Gsk3 are known in the art as described, e.g., in Hagen et al (2002), *J Biol Chem,* 277 (26):23330-23335, which describes a Gsk3 comprising a R96A mutation.

In some embodiments, the Wnt/β-catenin signaling pathway is activated by inhibiting Gsk3 in pluripotent stem cells by contacting the pluripotent stem cells with a small molecule that inhibits Gsk3 phosphotransferase activity or Gsk3 binding interactions. Suitable small molecule Gsk3 inhibitors include, but are not limited to, CHIR 99021, CHIR 98014, BIO-acetoxime, BIO, LiCl, SB 216763, SB 415286, AR A014418, 1-Azakenpaullone, Bis-7-indolylmaleimide, and any combinations thereof. In some embodiments, any of CHIR 99021, CHIR 98014, and BIO-acetoxime are used to inhibit Gsk3 in pluripotent stem cells in the differentiation methods described herein. In one embodiment, the small molecule Gsk3 inhibitor to be used is CHIR99021 at a concentration ranging from about 5 μM to about 20 μM, e.g., about 6 μM, 8 μM, 10 μM, 12 μM, 14 μM, 16 μM, or another concentration of CHIR99021 from about 5 μM to about 20 In another embodiment, the small molecule Gsk3 inhibitor to be used is CHIR 98014 at a concentration ranging from about 0.2 μM to about 2 μM, e.g., about 0.6 μM, 0.8 μM, 1 μM, 1.2 μM, 1.4 μM, 1.6 μM, or another concentration of CHIR99021 from about 0.2 μM to about 2 μM.

In other embodiments, Gsk3 activity is inhibited by RNA interference knockdown of Gsk3. For example, Gsk3 expression levels can be knocked-down using commercially available siRNAs against Gsk3, e.g., SignalSilence GSK-3α/β siRNA (catalog #6301 from Cell Signaling Techology®, Danvers, Mass.), or a retroviral vector with an inducible expression cassette for Gsk3, e.g., a commercially available Tet-inducible retroviral RNAi system from Clontech (Mountainview, Calif.) Catalog No. 630926, or a cumate-inducible system from Systems Biosciences, Inc. (Mountainview, Calif.), e.g., the SparQ® system, catalog no. QM200PA-2. In other embodiments, the Wnt/β-catenin signaling pathway is activated by overexpressing β-catenin itself, e.g., human β-catenin (GenBank Accession Nos: X87838 and CAA61107.1 for nucleotide and protein sequences, respectively). In one embodiment, β-catenin overexpression is inducible β-catenin overexpression achieved using, e.g., any of the just-mentioned inducible expression systems. Alternatively, a constitutively active, stabilized isoform of β-catenin is used, which contains point mutations S33A, S37A, T41A, and S45A as described, e.g., in Baba et at (2005), *Immunity,* 23(6):599-609.

In yet other embodiments, Wnt/β-catenin signaling pathway activation in pluripotent stem cell is achieved by contacting the cells with an agent that disrupts the interaction of β-catenin with Axin, a member of the β-catenin destruction complex. Disruption of Axin-β-catenin interaction allows β-catenin to escape degradation though the destruction complex thereby increasing the net level of β-catenin to drive β-catenin signaling. For example, the Axin-β-catenin interaction can be disrupted in pluripotent cells by contacting them with the compound 5-(Furan-2-yl)-N-(3-(1H-imidazol-1-yl)propyl)-1,2-oxazole-3-carboxamide ("SKL2001"), which is commercially available, e.g., as catalog no. 681667 from EMD4 Biosciences. An effective concentration of SKL2001 to activate Wnt/β-Catenin signaling ranges from about 10 μM to about 100 about 20 μM, 30 μM, 40 μM, 50 μM, 60 μM, 70 μM, 80 μM, 90 μM or another concentration of SKL2001 from about 10 μM to about 100 μM.

Inhibition of Wnt/β-Catenin Signaling

Inhibition of Wnt/β-catenin pathway signaling means inhibition of TCF/LEF-β-catenin mediated gene transcription Inhibition of Wnt/β-catenin pathway signaling can be achieved in a variety of ways including, but not limited to: providing small molecule inhibitors, RNA interference of, or blocking antibodies against functional canonical Wnt ligands or Wnt pathway receptors (e.g., Frizzled and LRP5/6); providing small molecules that promote degradation of β-catenin and/or TCF/LEF; gene interference knockdown of β-catenin and/or TCF/LEF; overexpression of a dominant negative form of β-catenin lacking the sequence for binding to TCF/LEF; overexpressing Axin2 (which increases β-catenin degradation); providing a small molecule inhibitor of a TCF/LEF and β-catenin interaction; and providing a small molecule inhibitor of a TCF/LEF-β-catenin and DNA promoter sequence interaction.

In some cases, inhibition of Wnt/β-catenin pathway signaling in a first cell population comprising cells expressing mesendodermal or mesodermal markers is achieved by contacting the first cell population with one or more small molecule inhibitors of a Wnt ligand (e.g., a small molecule that inhibit secretion of the Wnt ligand) o or inhibit Wnt ligands and their corresponding receptors interaction. Suitable small molecule inhibitors include, but are not limited to, N-(6-Methyl-2-benzothiazolyl)-2-[(3,4,6,7-tetrahydro-4-oxo-3-phenylthieno[3,2-d]pyrimidin-2-yl)thio]-acetamide ("IWP2") available commercially, e.g., as Sigma catalog no. IO536; 2-(3,4,6,7-tetrahydro-3-(2-methoxyphenyl)-4-oxothieno[3,2-d]pyrimidin-2-ylthio)-N-(6-methylbenzo[d]thiazol-2-yl)acetamide ("IWP4") available commercially, e.g., as catalog no. 04-00306 from Stemgent (San Diego, Calif.); 4-(1,3,3a,4,7,7a-Hexahydro-1,3-dioxo-4,7-methano-2H-isoindol-2-yl)-N-8-quinolinyl-Benzamide ("IWR-1") available commercially, e.g., as Sigma catalog no. I0161; Benzoic acid, 2-phenoxy-, 2-[(5-methyl-2-furanyl)methylene]hydrazide ("PNU-74654"), e.g., Sigma catalog no. P0052; or a combination thereof.

In some embodiments, the first population of cells is contacted with one or more small molecule compounds that promote degradation of β-catenin. In some cases, such small molecule compounds are compounds that, directly or indirectly, stabilize Axin, which is a member of the β-catenin destruction complex, and thereby enhance degradation of β-catenin. Examples of Axin-stabilizing compounds include, but are not limited to, 3,5,7,8-Tetrahydro-2-[4-

(trifluoromethyl)phenyl]-4H-thiopyrano[4,3-d]pyrimidin-4-one ("XAV939"), e.g., Sigma catalog no. X3004; 4-(1,3,3a,4,7,7a-Hexahydro-1,3-dioxo-4,7-methano-2H-isoindol-2-yl)-N-8-quinolinyl-Benzamide ("IWR-1") available commercially, e.g., as Sigma catalog no. I0161. In some cases, such small molecule compounds that, directly or indirectly, activate casein kinase 1α (CK1), which is a member of the β-catenin destruction complex, and thereby enhances degradation of β-catenin. Examples of CK1-stabilizing compounds include, but are not limited to, 6-(Dimethylamino)-2-[2-(2,5-dimethyl-1-phenyl-1H-pyrrol-3-yl)ethenyl]-1-methyl-4,4'-methylenebis[3-hydroxy-2-naphthalenecarboxylate](2:1)-quinolinium ("Pyrvinium pamoate salt hydrate"), e.g., Sigma catalog no. P0027.

A suitable working concentration range for such small molecule inhibitors is from about 0.1 µM to about 100 µM, e.g., about 2 µM, 5 µM, 7 µM, 10 µM, 12 µM, 15 µM, 18 µM, or another working concentration of one or more the foregoing small molecule inhibitors ranging from about 0.1 µM to about 100 µM. In one embodiment, IWP2 or IWP4 are used at a working concentration of about 5 µM. In other embodiments, the above-mentioned small molecule inhibitors are used at the corresponding target $IC_{50}$.

In other embodiments, inhibition of Wnt/β-catenin pathway signaling in the first cell population is enabled by RNA interference to decrease the expression of one or more targets in the Wnt/β-catenin pathway. For example in some cases, RNA interference is against β-catenin itself. In one embodiment, where one or more short hairpin interfering RNAs (shRNAs) are to be used to knock down β-catenin expression, at least one of the following shRNA sequences are used: (SEQ ID NO:63) 5'-CCGGAGGTGCTATCT-GTCTGCTCTACTCGAGTAGAGCAGACAGATAGCAC-CTTTTT T-3' or (SEQ ID NO:64) 5'-CCGGGCTTGGAAT-GAGACTGCTGATCTCGAGATCAGCAGTCTCAT TCCAAGCTTTTT-3'. Such shRNAs may be transfected as synthetic shRNAs into the first cell population by a number of standard methods known in the art. Alternatively, shRNA sequences may be expressed from an expression vector, e.g., from a plasmid expression vector, a recombinant retrovirus, or a recombinant lentivirus.

In some embodiments, the first cell population is generated from a genetically modified pluripotent stem cell line comprising an inducible expression cassette for expression of an interfering RNA, e.g., an shRNA against β-catenin, as exemplified herein. The use of an inducible expression cassette allows temporal control of β-catenin knockdown. Such temporal control is well suited to the timing of Wnt/β-catenin signaling inhibition used in the differentiation methods described herein.

As an alternative method for inhibiting Wnt/β-catenin signaling in the first cell population, the first cell population is contacted with at least one antibody that blocks activation of a Wnt ligand receptor. In some embodiments, the at least one antibody binds to one or more Wnt ligand family members and inhibits binding of the one or more Wnt ligands to their receptors. Such antibodies are known in the art, as described in, e.g. an anti-Wnt-1 antibody described in He et at (2004), *Neoplasia*, 6(1):7-14. In other embodiments, the blocking antibody is targeted against a Wnt ligand receptor and blocks the interaction of Wnt ligands with the receptor, as described, e.g., in Gurney et al (2012), *Proc. Natl. Acad. Sci. USA*, 109(29):11717-11722.

Culture Media

Defined media and substrate conditions for culturing pluripotent stem cells, as used in the methods described herein, are well known in the art. In some exemplary embodiments, pluripotent stem cells to be differentiated according to the methods disclosed herein are cultured in mTESR-1® medium (StemCell Technologies, Inc., Vancouver, Calif.), or Essential 8® medium (Life Technologies, Inc.) on a Matrigel® substrate (BD Biosciences, NJ) according to the manufacturer's protocol or on a Corning® Synthemax surface.

Upon initiating the first step and throughout the differentiation methods provided herein, pluripotent cells are typically cultured in a medium substantially free of insulin. In some embodiments, a medium comprising the supplement B-27 (minus insulin) (Life Technologies, catalog no. 0050129SA) is used throughout the differentiation process. In one embodiment, the medium used for differentiation method comprises the following components components: 0.1 mg/ml Apo-transferrin, 30 µM Sodium selenite, 0.02 µg/ml Progesterone, 16 µg/ml Putrescine, and 50 µg/ml BSA (termed "L5" herein). In some embodiments, the cell culture media used for the differentiation methods described herein are substantially free of Activin. In other embodiments, the medium used in the step (i) includes about 100 ng/ml Activin.

A number of known base culture media are suitable for use throughout the differentiation methods described herein. Such cell base cell culture media include, but are not limited to, RPMI, DMEM/F12 (1:3), DMEM/F12 (1:1), DMEM/F12 (3:1), F12, DMEM, and MEM.

In one embodiment, the cell culture medium used is RPMI supplemented with B27 (minus insulin). In another embodiment, the cell culture medium used is RPMI supplemented with L5. In yet another embodiment, the cell culture medium used is DMEM/F12 (1:3) supplemented with B27 (minus insulin).

The invention will be more fully understood upon consideration of the following non-limiting Examples. It is specifically contemplated that the methods disclosed are suited for pluripotent stem cells generally. All papers and patents disclosed herein are hereby incorporated by reference as if set forth in their entirety.

EXAMPLES

Example 1

Experimental Procedures

Maintenance of hPS Cells:

Transgene free human iPSCs (6-9-9 and 19-9-11) (Yu et al., Science 324, 797-801 (2009)), lentiviral integrated human iPSC (IMR90C4) (Yu et al., Science 318, 1917-1920 (2007)) and hESCs (H1, H7, H9) (Thomson et al., Science 282, 1145-1147 (1998)) were maintained on MEF feeders in hESC medium: DMEM/F12 culture medium supplemented with 20% KnockOut serum replacer, 0.1 mM non-essential amino acids, 1 mM L-glutamine (all from Invitrogen), 0.1 mM β-mercaptoethanol (Sigma) and 10 ng/ml human bFGF (Invitrogen). For feeder free culture, hPS cells were maintained on Matrigel® (BD Biosciences) or Synthemax plates (Corning) in mTeSR1 medium.

Cardiac Differentiation Via EBs:

hPS cells were passaged onto MEFs (~13,000 cells/cm$^2$) and cultured in hESC medium for 2 days followed by another 3 days in hESC medium supplemented with BIO (Sigma) or CHIR99021 (Selleck). To form EBs, hPS cell aggregates generated by dispase treatment were cultured in low-attachment plates overnight in RPMI plus 20% KnockOut serum replacer. The next day, the EBs were cultured in EB20 (RPMI plus 20% FBS) for 4 days in suspension. EBs were then plated onto 0.1% gelatin-coated 6-well culture plates at 50-100 EBs/well, and cultured in EB20 medium. After 10 days of differentiation, the FBS concentration was reduced to 2% EB2 (RPMI plus 2% FBS). The number of contracting EBs was visually assessed using a microscope with a 37° C. heated stage.

Cardiac Directed Differentiation Using Activin a and BMP4:

hPS cells maintained on Matrigel® in mTeSR1 were dissociated into single cells with Accutase (Invitrogen) at 37° C. for 5 min and then seeded onto a Matrigel®-coated cell culture dish at 100,000 cell/cm$^2$ in mTeSR1 supplemented with 5 µM ROCK inhibitor (Y-27632, Stemgent) (day −5). Cells were cultured in mTeSR1, changed daily. At day 0, cells were treated with 100 ng/ml Activin A (R&D) in RPMI/B27-insulin. After 24 hr, the medium was changed to RPMI/B27-insulin supplemented with 5 ng/ml BMP4 (R&D) for another 4 days. At day 5, the medium was changed with RPMI/B27-insulin. At day 7 the cells were transferred to RPMI/B27, and medium changed every 3 days. When using GSK3 inhibitors to stimulate differentiation, cells were cultured in mTeSR1 containing BIO or CHIR99021 from day −3 to day 0.

Cardiac Directed Differentiation Via Small Molecules:

Cells were dissociated and plated as described in the Activin/BMP4 protocol. When hPS cells maintained on Matrigel® or Synthemax plates achieved confluence, cells were treated with CH in RPMI/B27-insulin for 24 hr (day 0 to day 1). The medium was changed to RPMI/B27-insulin, followed by 2 µg/ml dox treatment at different times between day 1 and day 5 for transgenic cell lines. For genetically unmodified lines, 5 µM IWP2 (Tocris) or IWP4 (Stemgent) was added at day 3 and removed during the day 5 medium change. Cells were maintained in the RPMI/B27 starting from day 7, with the medium changed every 3 days.

Lentiviral Production and Infection of hPS Cells:

The pLKO.1 based constitutive knockdown of β-catenin vectors shcat-1 and shcat-2 (Addgene plasmids 19761 and 19762) and inducible knockdown β-catenin vectors ishcat-1 and ishcat-2 (Biosettia) were used for lentivirus particle production. These vectors were cotransfected with the helper plasmids psPAX2 and pMD2.G (Addgene plasmids 12260 and 12259) into HEK-293TN cells (System Biosciences) for virus production. Virus-containing media were collected at 48 and 72 hr after transfection and used for hPS cell infection in the presence of 6 µg/ml polybrene (Sigma). Transduced cells were selected and clonally isolated based on resistance to 1 µg/ml puromycin.

RT-PCR and Quantitative RT-PCR:

Total RNA was prepared with the RNeasy mini kit (QIAGEN) and treated with DNase (QIAGEN).1 µg RNA was reverse transcribed into cDNA via Oligo (dT) with Superscript III Reverse Transcriptase (Invitrogen). Real-time quantitative PCR was done in triplicate with iQ SYBR Green SuperMix (Bio-Rad). RT-PCR was done with Gotaq Master Mix (Promega) and then subjected to 2% agarose gel electrophoresis. ACTB was used as an endogenous control. Primer sequences are set forth in Table 1.

TABLE 1

Primers for RT-PCR and Q-PCR

| Genes | Sequences (5' - 3') | SEQ ID NO: | Size/Tm/Cycle |
|---|---|---|---|
| OCT4 | F: CAGTGCCCGAAACCCACAC | 1 | 161/58/30 |
|  | R: GGAGACCCAGCAGCCTCAAA | 2 |  |
| NANOG | F: CGAAGAATAGCAATGGTGTGACG | 3 | 328/58/30 |
|  | R: TTCCAAAGCAGCCTCCAAGTC | 4 |  |
| SOX2 | F: CAAGATGCACAACTCGGAGA | 5 | 300/58/30 |
|  | R: GTTCATGTGCGCGTAACTGT | 6 |  |
| CTNNB1 | F: GAATGAGACTGCTGATCTTGGAC | 7 | 250/58/30 |
|  | R: CTGATTGCTGTCACCTGGAG | 8 |  |
| GSC | F: CGAGGAGAAAGTGGAGGTCTG G | 9 | 261/55/35 |
|  | R: GCAGCGCGTGTGCAAGAAA | 10 |  |
| MIXL1 | F: CAGAGTGGGAAATCCTTCCA | 11 | 231/58/35 |
|  | R: TGAGTCCAGCTTTGAACCAA | 12 |  |
| T | F: CTTCCCTGAGACCCAGTTCA | 13 | 289/58/35 |
|  | R: CAGGGTTGGGTACCTGTCAC | 14 |  |
| MSX1 | F: CCGAGAGGACCCCGTGGATGC | 15 | 280/58/35 |
|  | R: GCCTCTTGTAGTCTCTTTGCC | 16 |  |
| ISL1 | F: CACAAGCGTCTCGGGATT | 17 | 202/58/40 |
|  | R: AGTGGCAAGTCTTCCGACA | 18 |  |
| WNT3A | F: GCCCCACTCGGATACTTC T | 19 | 189/58/40 |
|  | R: GGCATGATCTCCACGTAGT | 20 |  |
| WNT8A | F: ACAGGTCCCAAGGCCTATCT | 21 | 335/58/40 |
|  | R: ATCCTTTCCCCAAATTCCAC | 22 |  |
| NKX2-5 | F: GCGATTATGCAGCGTGCAATGAGT | 23 | 220/58/35 |
|  | R: AACATAAATACGGGTGGGTGCGTG | 24 |  |
| GATA4 | F: TCCAAACCAGAAAACGGAAG | 25 | 352/58/40 |
|  | R: AAGACCAGGCTGTTCCAAGA | 26 |  |

TABLE 1-continued

Primers for RT-PCR and Q-PCR

| Genes | Sequences (5' - 3') | SEQ ID NO: | Size/Tm/Cycle |
|---|---|---|---|
| MEF2C | F: AGCCCTGAGTCTGAGGACAA<br>R: GTGAGCCAGTGGCAATAGGT | 27<br>28 | 195/58/40 |
| TBX5 | F: GAAACCCAGCATAGGAGCTG<br>R: CAGCCTCACATCTTACCCTGT | 29<br>30 | 191/58/40 |
| TBX2 | F: AGTGGATGGCTAAGCCTGTG<br>R: ACGGGTTGTTGTCGATCTTC | 31<br>32 | 249/58/40 |
| TNNI3 | F: CTGCAGATTGCAAAGCAAGA<br>R: CCTCCTTCTTCACCTGCTTG | 33<br>34 | 379/58/40 |
| TNNT2 | F: TTCACCAAAGATCTGCTCCTCGCT<br>R: TTATTACTGGTGTGGAGTGGGTGTGG | 35<br>36 | 165/58/40 |
| MYL7 | F: GAGGAGAATGGCCAGCAGGAA<br>R: GCGAACATCTGCTCCACCTCA | 37<br>38 | 449/58/35 |
| MYL2 | F: ACATCATCACCCACGGAGAAGAGA<br>R: ATTGGAACATGGCCTCTGGATGGA | 39<br>40 | 164/58/40 |
| PLN | F: ACAGCTGCCAAGGCTACCTA<br>R: GCTTTTGACGTGCTTGTTGA | 41<br>42 | 191/58/40 |
| CD31 | F: GCTGACCCTTCTGCTCTGTT<br>R: TGAGAGGTGGTGCTGACATC | 43<br>44 | 238/55/35 |
| NODAL | F: CTTCCTGAGCCAACAAGAGG<br>R: AGGTGACCTGGGACAAAGTG | 45<br>46 | 197/58/40 |
| BMP2 | F: TCAAGCCAAACACAAACAGC<br>R: ACGTCTGAACAATGGCATGA | 47<br>48 | 197/58/40 |
| BMP4 | F: TGAGCCTTTCCAGCAAGTTT<br>R: CTTCCCCGTCTCAGGTATCA | 49<br>50 | 180/58/40 |
| NOGGIN | F: TCAACACCCAGACCCTATC<br>R: TGTAACTTCCTCCGCAGCTT | 51<br>52 | 298/58/40 |
| GAPDH | F: CCCCTTCATTGACCTCAACTACA<br>R: TTGCTGATGATCTTGAGGCTGT | 53<br>54 | 342/58/30 |
| ACTB | F: CCTGAACCCTAAGGCCAACCG<br>R: GCTCATAGCTCTTCTCCAGGG | 55<br>56 | 400/58/30 |
| Primers for quantitative RT-PCR | | | |
| GAPDH | F: GTGGACCTGACCTGCCGTCT<br>R: GGAGGAGTGGGTGTCGCTGT | 57<br>58 | 152 |
| T | F: AAGAAGGAAATGCAGCCTCA<br>R: TACTGCAGGTGTGAGCAAGG | 59<br>60 | 101 |
| CTNNB1 | F: CCCACTAATGTCCAGCGTTT<br>R: AACGCATGATAGCGTGTCTG | 61<br>62 | 217 |

Flow Cytometry:

Cells were dissociated into single cells and then fixed with 1% paraformaldehyde for 20 min at room temperature and stained with primary and secondary antibodies in PBS plus 0.1% Triton X-100 and 0.5% BSA. For the cell proliferation assay, a 17-hour pulse of BrdU was performed to identify dividing cardiomyocytes (Zhang et al., Circ. Res. 104, e30-41 (2009)). Data were collected on a FACSCaliber flow cytometer (Beckton Dickinson) and analyzed using FlowJo. Antibodies are set forth in Table 2.

TABLE 2

Antibodies for immunostaining (IS), western blotting (WB) and flow cytometry (FC).

| Antibody | | Application |
|---|---|---|
| Actin, Smooth muscle | Lab Vision; mouse IgG2a, Clone: 1A4; Ms-113-p | 1:100 (FC) |
| Cardiac Troponin T | Lab Vision; mouse IgG1; Clone: 13-11; ms-295-pl | 1:200 (FC) |

TABLE 2-continued

Antibodies for immunostaining (IS), western blotting (WB) and flow cytometry (FC).

| Antibody | | Application |
|---|---|---|
| MF20 | Developmental Studies Hybridoma Bank; mouse IgG2b | 1:20 (FC) |
| MLC2v | ProteinTech Group; Rabbit polyclonal; PTG10906-1-AP | 1:200 (FC) |
| MLC2a | Synaptic systems; mouse IgG2b, Clone: 56F5; Cat: 311011 | 1:200 (IS and FC) |
| α-actinin | Sigma; mouse IgG1; Clone: EA-53 | 1:500 (IS) |
| Brachyury | R&D; Polyclonal Ab, Goat IgG; Clone: AF2085 | 1:100 (FC) |
| ISL1 | DSHB; mouse IgG2b; Clone: 39.4D5-s | 1:20 (IS) |
| Oct-3/4 | Santa Cruz; Rabbit IgG; Clone: H-134; sc-9081 | 1:40 (FC) |
| Oct-3/4 | Santa Cruz; Mouse IgG$_{2b}$; Clone: C-10; sc-5279 | 1:100 (IS) |
| NKX2-5 | Santa Cruz; Rabbit IgG; Clone: H-114; sc-14033 | 1:75 (IS) |
| Ki67 | BD Bioscience; mouse IgG1; Cat: 550609 | 1:100 (FC) |
| BrdU | Invitrogen; mouse IgG1; PRB-1; Cat: A21300; Lot: 612217 | 1:100 (FC) |
| Phospho-Smad1/5 (Ser463/465) | Cell Signaling Technology; Rabbit mAb; 41D10; Cat: 9516S | 1:500 (WB) |
| Phospho-Smad2 (Ser465/467) | Cell Signaling Technology; Rabbit mAb; 138D4; 3108S | 1:500 (WB) |
| Smad1 | Cell Signaling Technology; Rabbit mAb; D59D7; 6944P | 1:1000 (WB) |
| Smad2/3 | Cell Signaling Technology; Rabbit IgG; Cat: 5678S | 1:1000 (WB) |
| BMP2/4 | Santa Cruz; mouse IgG2a; Clone H-1; sc-137087 | 1:500 (WB) |
| β-Actin | Cell Signaling Technology; Rabbit mAb (HRP Conjugate); 13E5; 5125S | 1:1000 (WB) |
| goat anti-mouse IgG-HRP | Santa Cruz, sc-2005 | 1:1000 (WB) |

Immunostaining:

Cells were fixed with 4% paraformaldehyde for 15 min at room temperature and then stained with primary and secondary antibodies in PBS plus 0.4% Triton X-100 and 5% non-fat dry milk (Bio-Rad). Nuclei were stained with Gold Anti-fade Reagent with DAPI (Invitrogen). An epifluorescence microscope (Leica DM IRB) with a QImaging® Retiga 4000R camera was used for imaging analysis. Antibodies are set forth in Table 2.

Western Blot Analysis:

Cells were lysed in M-PER Mammalian Protein Extraction Reagent (Pierce) in the presence of Halt Protease and Phosphatase Inhibitor Cocktail (Pierce). Proteins were separated by 10% Tris-Glycine SDS/PAGE (Invitrogen) under denaturing conditions and transferred to a nitrocellulose membrane. After blocking with 5% milk in TBST, the membrane was incubated with primary antibody overnight at 4° C. The membrane was then washed, incubated with an anti-mouse/rabbit peroxidase-conjugated secondary antibody (1:1000, Cell Signaling) at room temperature for 1 hr, and developed by SuperSignal chemiluminescence (Pierce). Antibodies are listed in Table 2.

Electrophysiology: Beating cardiomyocyte clusters were microdissected and replated onto glass coverslips and maintained in EB2 medium prior to recording. Action potential activity was assessed using glass microelectrodes (50-100 MΩ; 3 M KCl) in a 37° C. bath continuously perfused with Tyrode's solution (mmole/L): 140 NaCl, 5.4 KCl, 1.8 CaCl$_2$, 1 MgCl$_2$, 10 Hepes, 10 glucose, pH 7.4 NaOH). Junction potentials and capacitance were nulled and data acquired at 10 kHz with an AxoClamp2A amplifier and pClamp 9.2 software (Molecular Devices, Sunnyvale Calif.). Electrical field stimulation was performed using two platinum electrodes coupled to a Grass SD-9 stimulator (Quincy, Mass.). For analysis, data were filtered off-line using a low pass Gaussian filter with a cut-off frequency of 2 kHz.

Electron Microscopy:

Contracting areas were microdissected and re-plated onto gelatin coated glass coverslips. The clusters were fixed overnight at 4° C. in a 2.5% gluteraldehyde, 2% paraformaldehyde, 0.1 M cacodylate buffer solution and then post-fixed with 1% osmium tetroxide. Samples were dehydrated via an ethanol gradient and embedded in durcapan (Fluka). The glass coverslip was dissolved with hydrofluoric acid treatment. Ultrathin 60 nm sections were stained with uranyl acetate and lead citrate. Samples were visualized on a Phillips CM120 STEM.

Statistics:

Data are presented as mean±standard error of the mean (SEM). Statistical significance was determined by Student's t-test (two-tail) for two groups or one-way ANOVA for multiple groups with post hoc testing using Tukey method using Microcal Origin, v8.0. P<0.05 was considered statistically significant.

Example 2

Figure 1B:
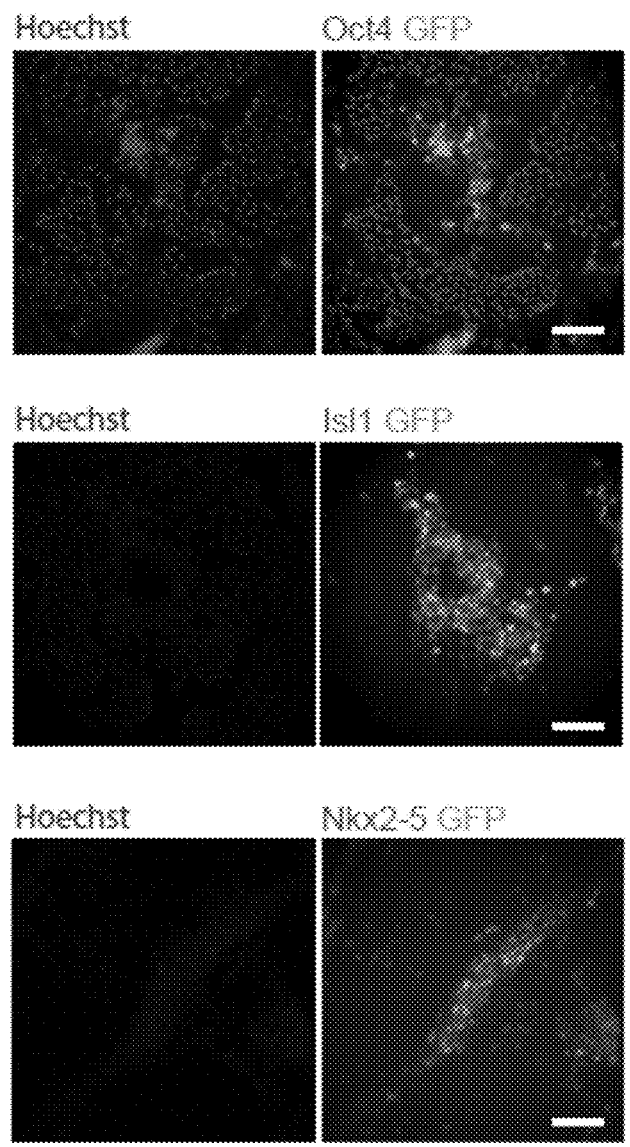
Figure 2A:
FIGS. 2A-E illustrate that treatment of hPS cells with Gsk3 inhibitors enhances cardiac differentiation.
Figure 2B:
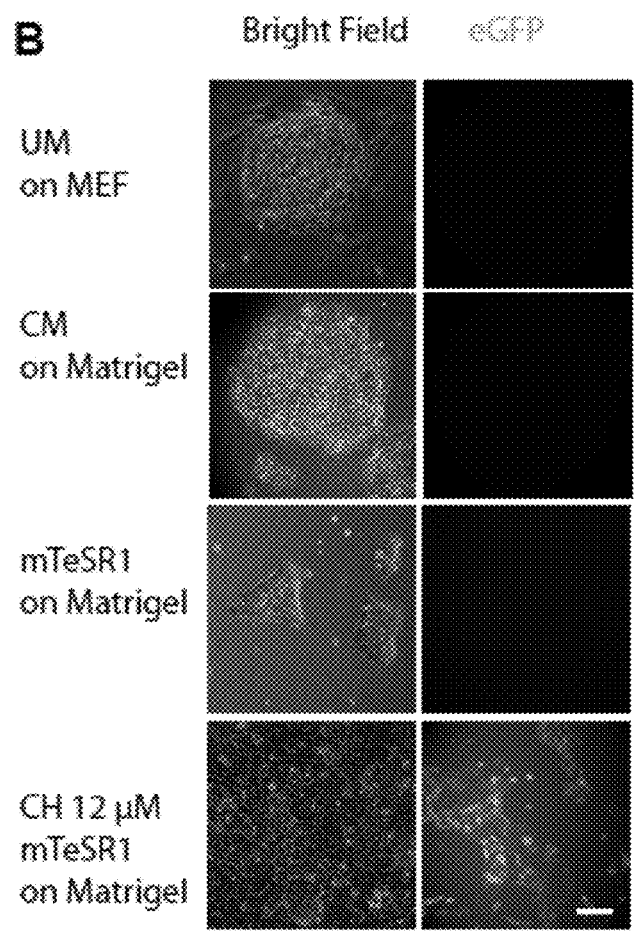
Figure 2C:
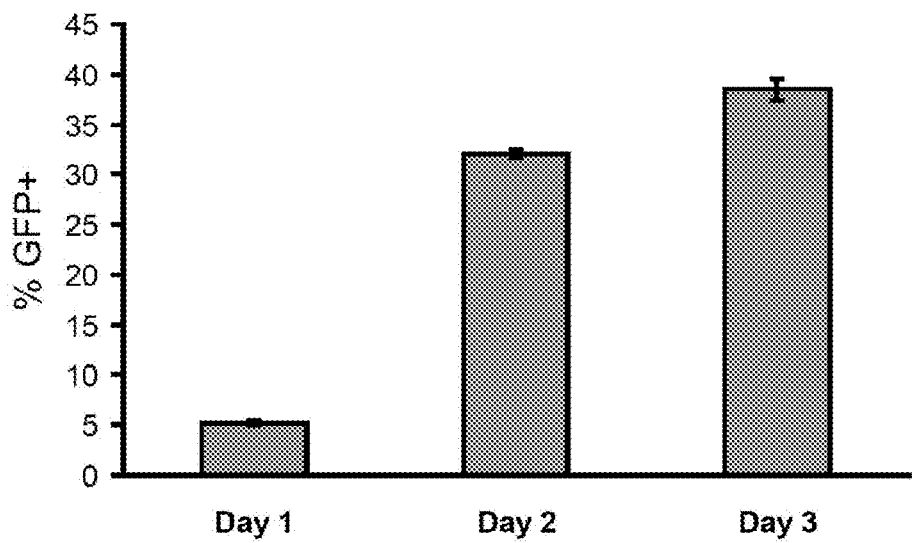
Figure 2C:
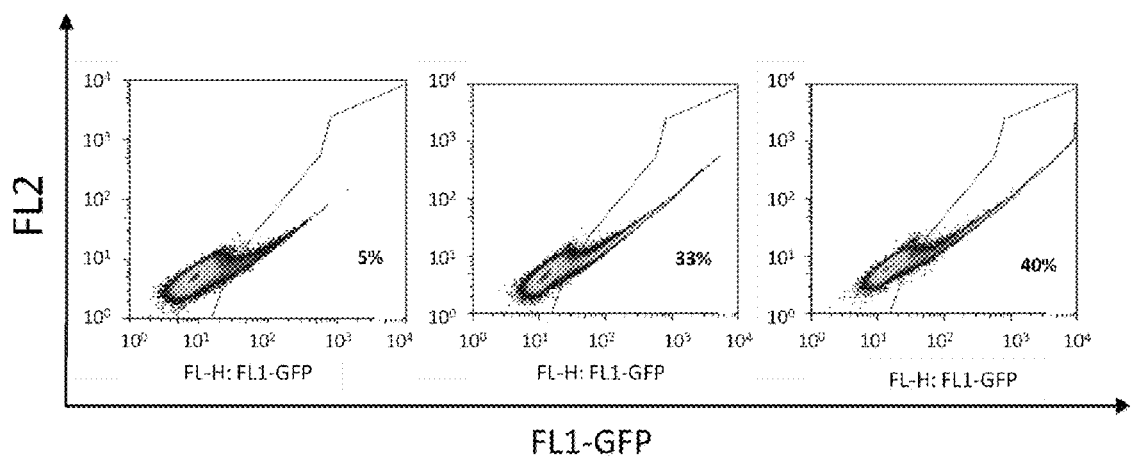
Figure 2D:
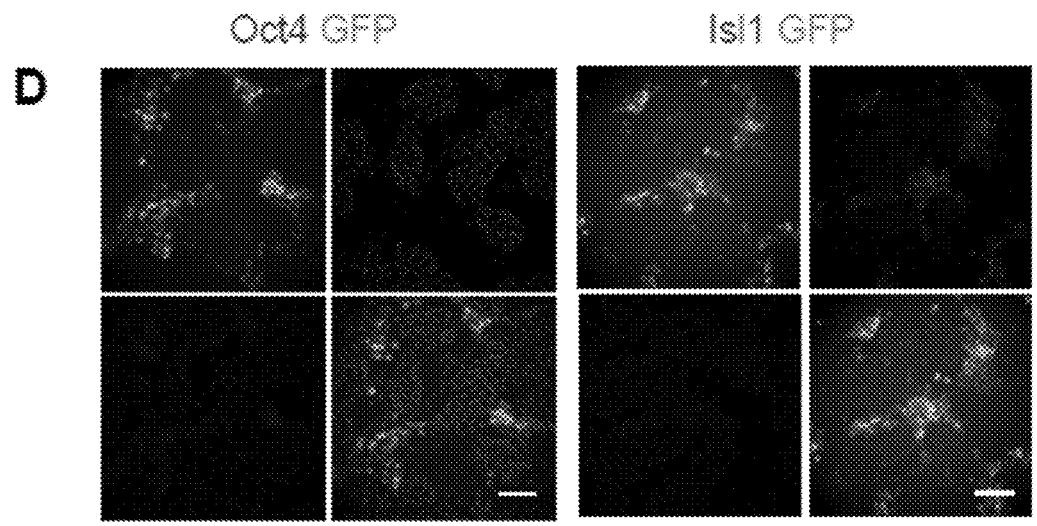

Wnt/β-Catenin Pathway Activation by Gsk3 Inhibitors Abrogates hPS Cell Self-Renewal and Enhances Cardiac Differentiation In order to probe the activation of canonical Wnt/β-catenin signaling during hPS cell specification to cardiomyocytes, the inventors generated a series of promoter-reporter cell lines in H1 and H9 hESC, and 19-9-11 human iPSC lines. These reporter lines, integrated with a lentiviral 7TGP vector, express GFP under control of a consensus TCF/LEF binding sequence promoter which reports β-catenin activation (FIG. 2A) (Fuerer and Nusse, PLoS One 5:e9370 (2010)). Whereas Wnt/β-catenin activation has been reported in undifferentiated mESCs and hESCs (Anton et al., FEBS Lett. 581:5247-5254 (2007); Sato et al., Nat. Med. 10:55-63 (2004); Takao et al., Biochem. Bioph. Res. Co. 353:699-705 (2007)), the inventors and others (Dravid et al., Stem Cells 23: 1489-1501 (2005)) failed to observe significant TCF/LEF-mediated transcriptional activity in self-renewing H9 hESCs in several different culture conditions, including mouse embryonic fibroblast (MEF) co-culture, in MEF conditioned medium (CM) on Matrigel®, and in mTeSR1 medium on Matrigel® (FIG. 2B). However, treatment of the H9-7TGP reporter line with the GSK3 inhibitor CHIR99021 (CH) (Ying et al., Nature 453:519-U515 (2008)) activated TCF/LEF promoter activity in a CH concentration-dependent manner (FIG. 1A; data represent the mean±SEM of 3 experiments). Approximately 50% of H9-7TGP cells expressed GFP at 4 days post-addition of 15 μM CH. Similar results were obtained following CH treatment of WNT reporter line H1-7TGP (FIG. 2C). Immunofluorescent analysis revealed that the CH-induced H9-7TGP GFP+ cells did not express Oct4, but did express Isl1 and Nkx2.5 (FIG. 1B). Similar results were obtained in the 19-9-11 7TGP iPSC line (FIG. 2D), suggesting commitment of this GFP+ cell population to the early cardiomyocyte lineage.

Figure 1C:
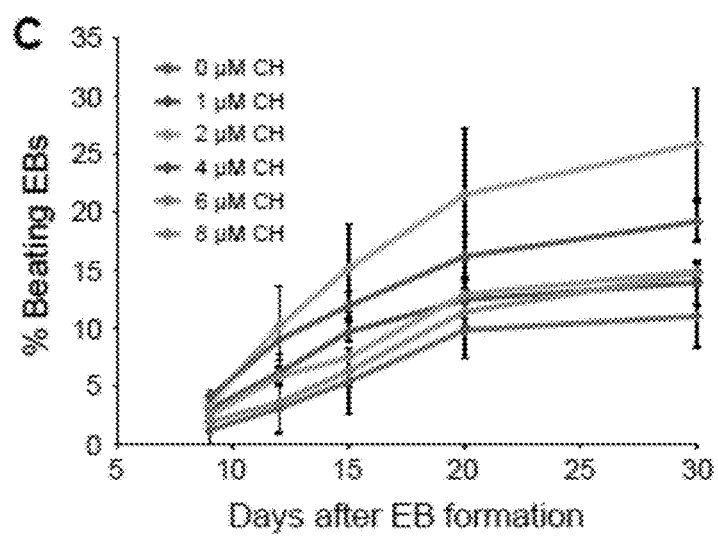
Figure 1D:
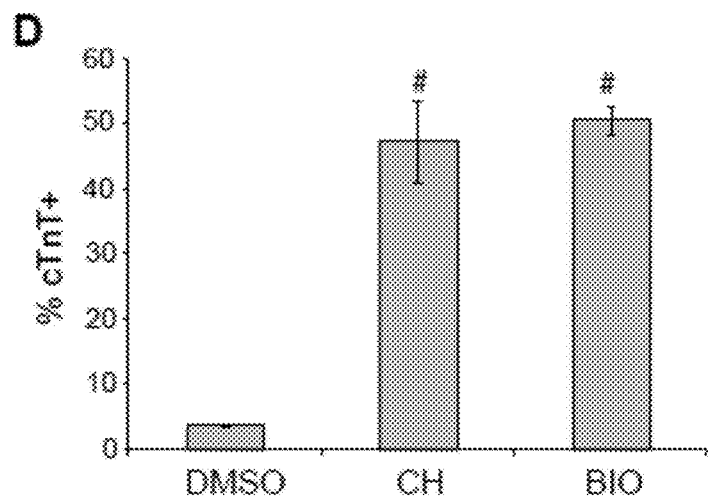
Figure 2E:
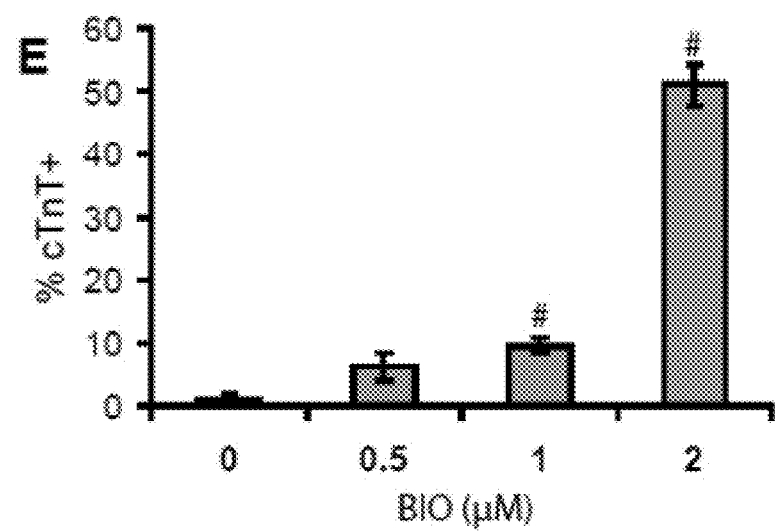

Since GSK3 inhibition did not support pluripotency of hPS cells but instead induced differentiation toward cardiac lineages, the inventors quantitatively assessed the effect of incorporating GSK3 inhibitors during previously reported embryoid body (EB) and modified Activin A/BMP directed differentiation protocols (Laflamme et al., Nat. Biotechnol. 25 (9):1015 (2007)). Undifferentiated H9 hESCs were cultured in the presence of 0-8 μM CH for three days prior to EB formation. EBs were cultured in suspension for 4 days before transferring to 0.1% gelatin coated plates. Visual analysis of spontaneously-contracting outgrowths indicated that the efficiency of cardiomyocyte differentiation peaked at 2-4 μM CH (FIG. 1C). The inventors also applied the GSK3 inhibitors CH and BIO to undifferentiated H9 hESCs three days prior to directed differentiation to cardiomyocytes via Activin A and BMP4. This protocol generated very few contracting cardiomyocytes in H9 cells. However, application of GSK3 inhibitors CH or BIO 3 days prior to addition of growth factors greatly enhanced cardiomyocyte generation, yielding an average of 50% cTNT-labeled cells (FIG. 1D; p<0.005, CH versus DMSO, BIO versus DMSO; t test). Three days of BIO pretreatment prior to addition of Activin A and BMP4 also enhanced generation of cTNT-expressing cells in the IMR90C4 iPSC line in a dose-dependent manner (FIG. 2E).

Example 3

Differentiation Induced by Gsk3 Inhibitor Treatment is β-Catenin Dependent

Figure 3A:
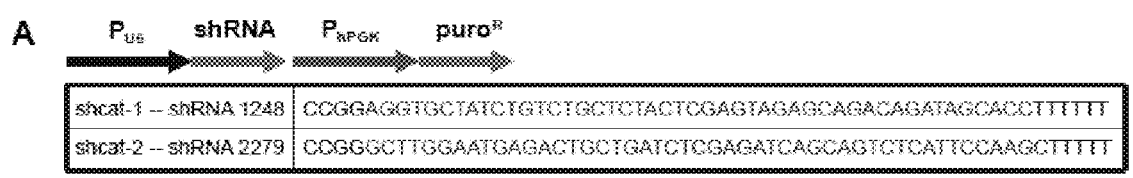
FIGS. 3A-D illustrate that differentiation induced by treatment with Gsk3 inhibitors is β-catenin dependent.
Figure 3B:
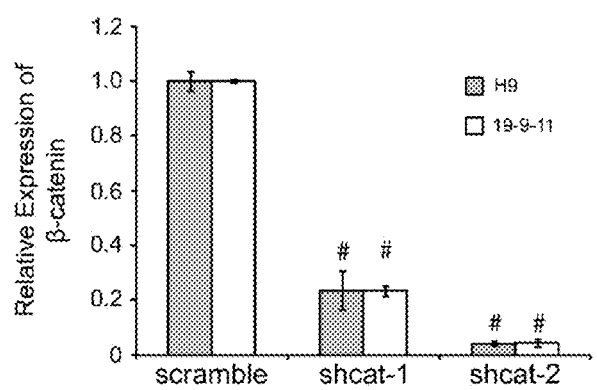
Figure 4A:
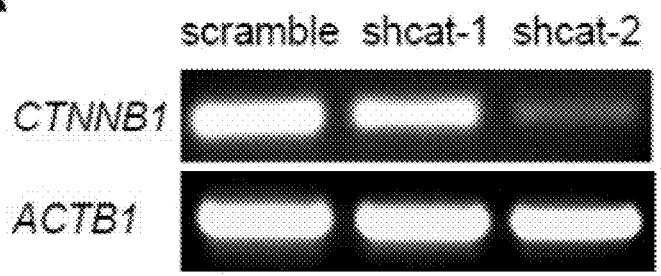
FIGS. 4A-G illustrate temporal modulation of Wnt/β-catenin signaling promoting cardiac differentiation.
Figure 4B:
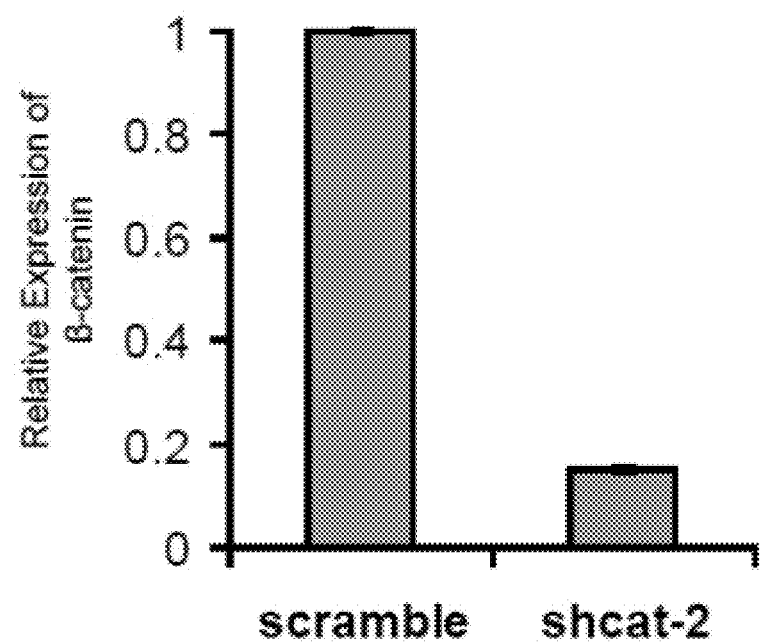
Figure 4C:
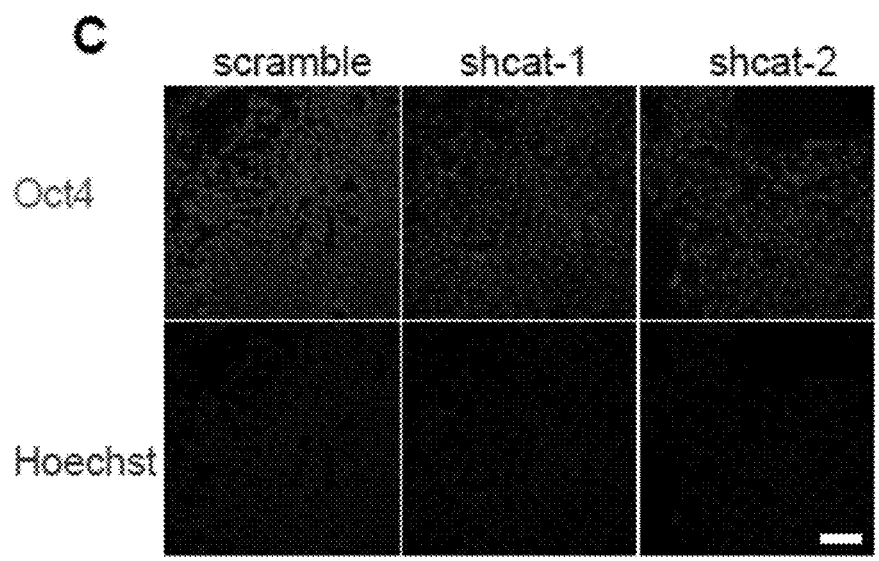
Figure 4D:
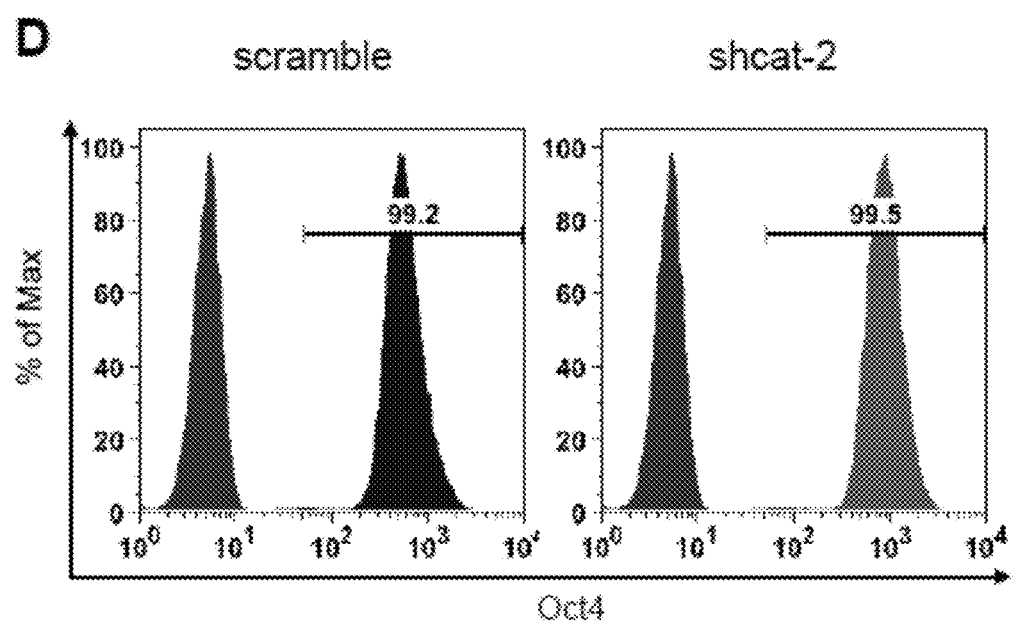
Figure 4E:
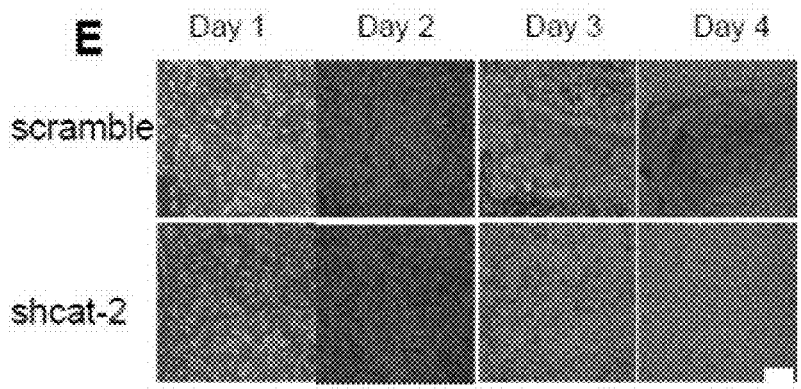

In order to more fully evaluate the role of canonical Wnt signaling in cardiomyocyte specification of hPS cells, the inventors generated H7, H9 and 19-9-11 iPSC clones carrying lentiviral integrated β-catenin shRNA and control scrambled sequences (FIG. 3A). Referring to FIG. 2A, $P_{U6}$ and $P_{hPGK}$ are human U6 and human PGK promoters, red and green sequences are forward and reverse shRNA sequence of β-catenin, and the blue sequence represents the loop sequence. The β-catenin knockdown efficiency of the shRNA knockdown lines compared to the scrambled lines was 77% for β-catenin shRNA sequence 1 (shcat-1) and 96% for sequence 2 (shcat-2) (FIGS. 3B, 4A and 4B). Knockdown of β-catenin did not abrogate hESC or iPSC self-renewal, as shown by Oct4 expression (FIGS. 4C and 4D).

Figure 3C:
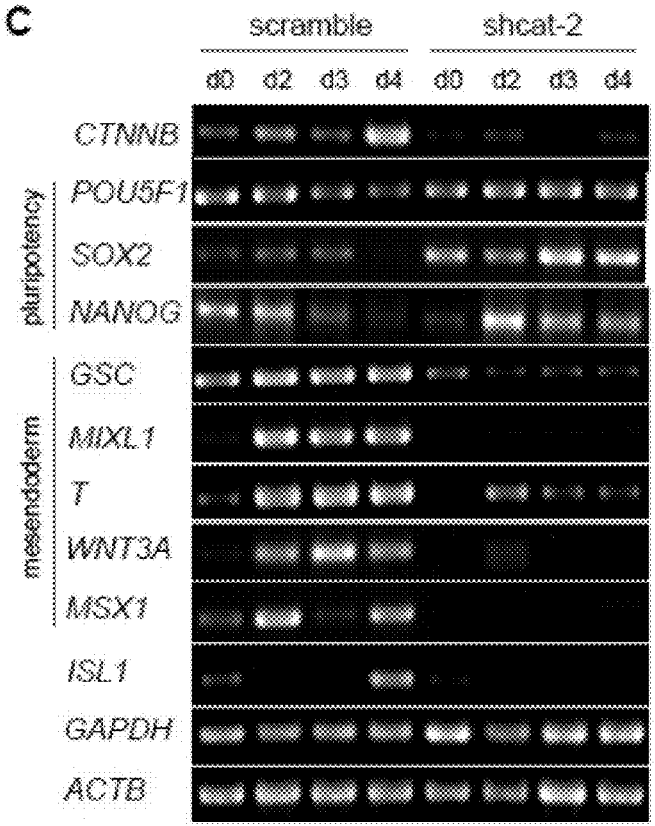
Figure 3D:
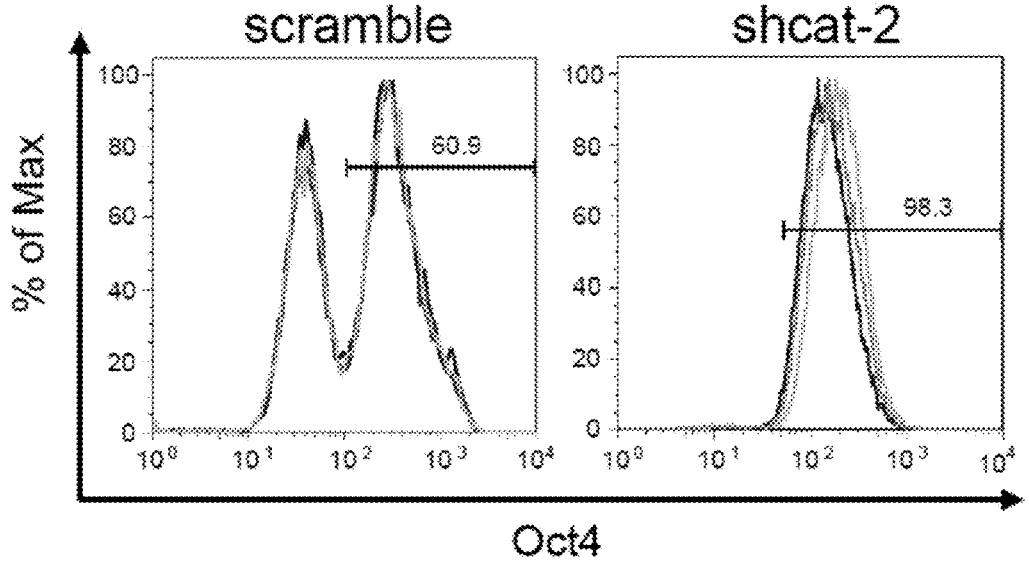
Figure 3E:
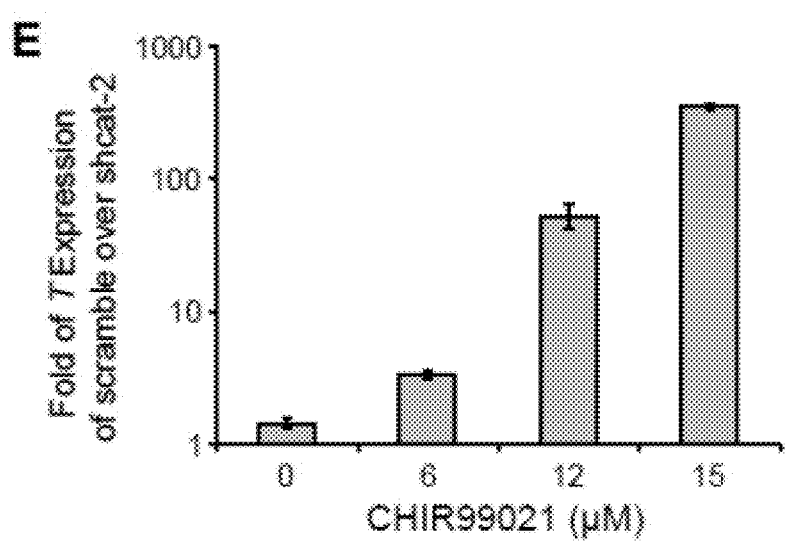
FIG. 3E depicts relative expression of Tln scramble and shcat-2 lines quantified by qPCR. 19-9-11 shcat-2 and scramble lines were cultured on Matrigel® in mTeSR1 containing CHIR99021 for 2 days.
Figure 3F:
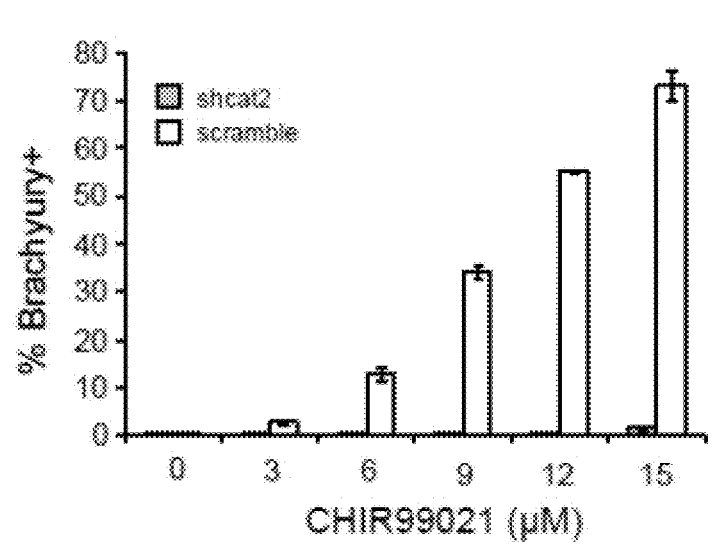
FIG. 3F depicts flow cytometry analysis of brachyury expression in 19-9-11 shcat-2 and scramble cells exposed to CH for 4 days. Error bars represent s.e.m. of 3 independent replicates.
Figure 3G:
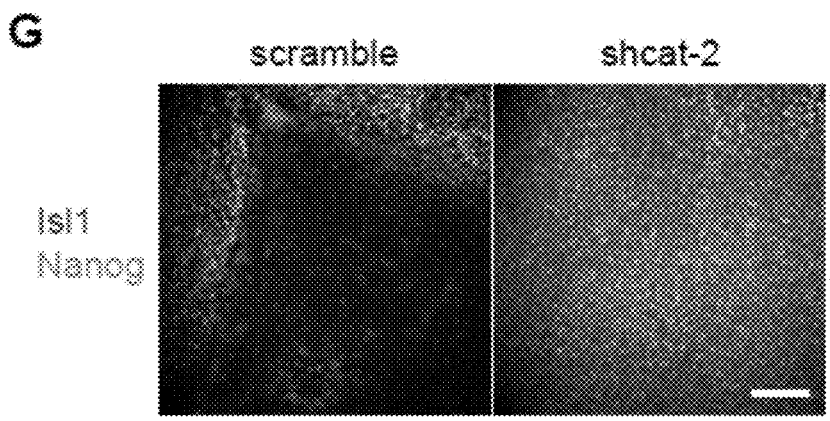
FIG. 3G depicts Nanog and Isl1 expression in 19-9-11 shcat-2 and scramble line cultured on Matrigel® in mTeSR1 containing 12 μM CH. Scale bar=50 μm.

To test whether induction of cardiomyocyte differentiation by GSK3 inhibitors requires β-catenin, the inventors treated the shcat-2 and scramble 19-9-11 lines with CH in mTeSR1 medium. While the shcat-2 line maintained an undifferentiated morphology, the scramble line appeared to undergo differentiation (FIG. 2E), similar to non-transduced lines treated with CH (FIGS. 1B and 2B). Induction of differentiation following CH treatment in the scramble control was further indicated by diminished SOX2 and NANOG expression at day 4 (FIG. 3C). No significant differences in expression of these genes were detected in shcat-2 cells treated with CH. After 4 days of CH treatment in mTeSR1, the percentage of cells expressing Oct4 decreased to 61% in the scramble line, while 98% of the shcat-2 cells expressed Oct4 (FIG. 3D). In addition, expression of mesendoderm and early mesoderm genes MIXL1, GSC, T, WNT3A and MSX1 emerged in CH-treated scramble cells but not CH-treated shcat-2 cells (FIG. 3C). To better understand early mesoderm induction via GSK3 inhibition, the inventors analyzed expression of the early mesoderm gene Tin scramble and shcat-2 19-9-11 lines. As CH concentration increased, the ratio of T expression in scramble to the shcat-2 line increased (FIG. 3E). Less than 2% of shcat-2 cells expressed brachyury upon exposure to different concentrations of CH treatment for 4 days. In contrast, the scramble line exhibited a CH concentration-dependent increase in the fraction of cells expressing brachyury, with 76% brachyury+ cells following 15 μM CH treatment for 4 days (FIG. 3F). In addition, immunostaining of the scramble cell line after 15 μM CH treatment in mTeSR1 for 4 days showed substantial numbers of Nanog−/Isl1+ cells while the shcat-2 cells treated with CH contained only Nanog+/Isl1− cells (FIG. 3G). Together these results demonstrate that treatment of undifferentiated hPS cells with GSK3 inhibitors induces mesoderm differentiation in a β-catenin dependent manner and that these mesodermal cells can differentiate to Isl1+ and Nkx2.5+(FIG. 1B) cardiomyocyte progenitors.

Example 4

Temporal Requirement of β-Catenin for Efficient Cardiac Differentiation

Figure 4F:
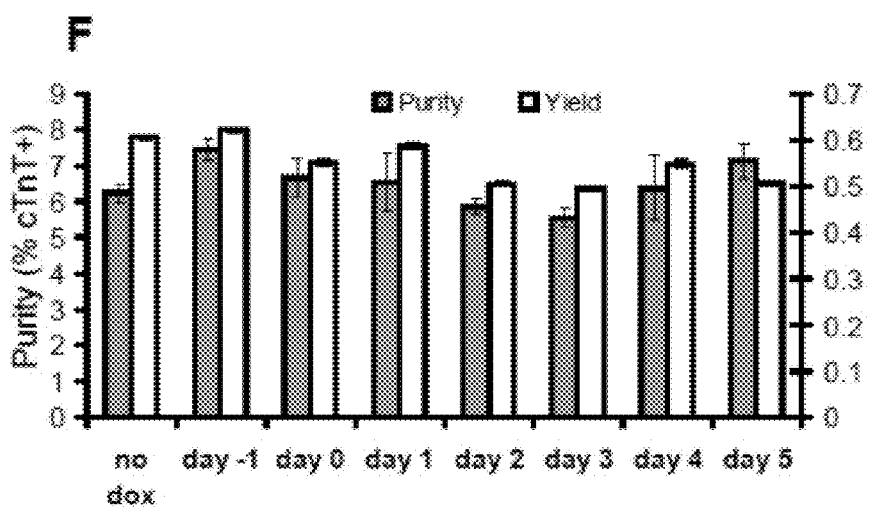
Figure 4G:
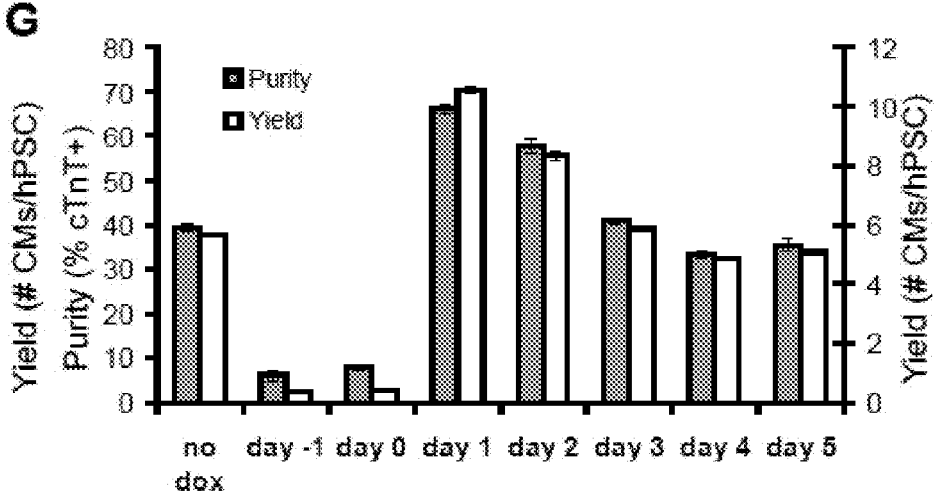
Figure 5A:
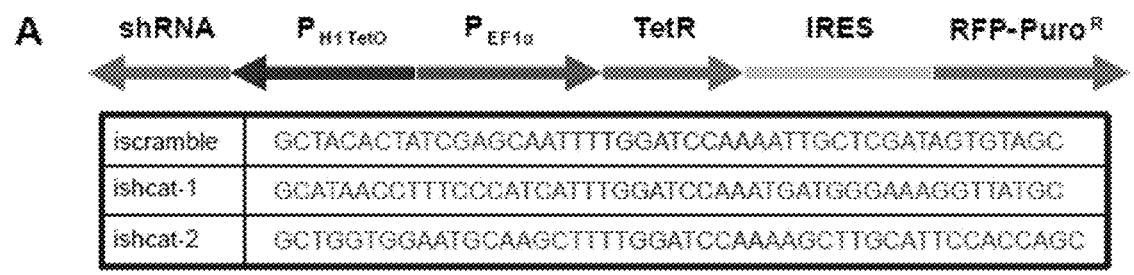
FIGS. 5A-D illustrate temporal inhibition of Wnt/β-catenin signaling promoting cardiac differentiation.
Figure 5B:
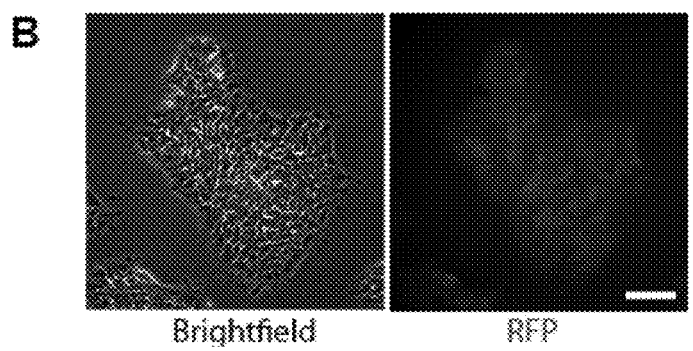
Figure 5C:
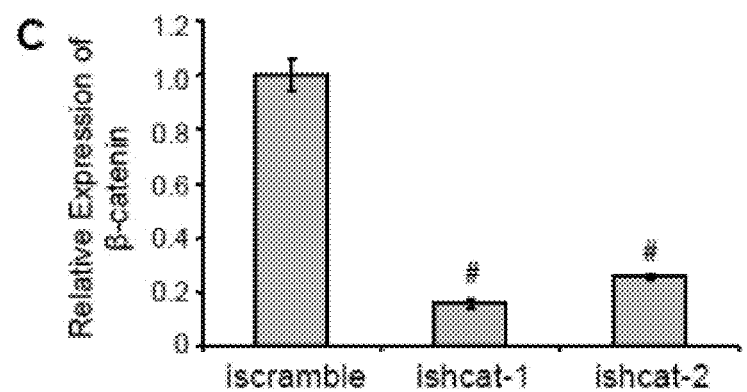
Figure 5D:
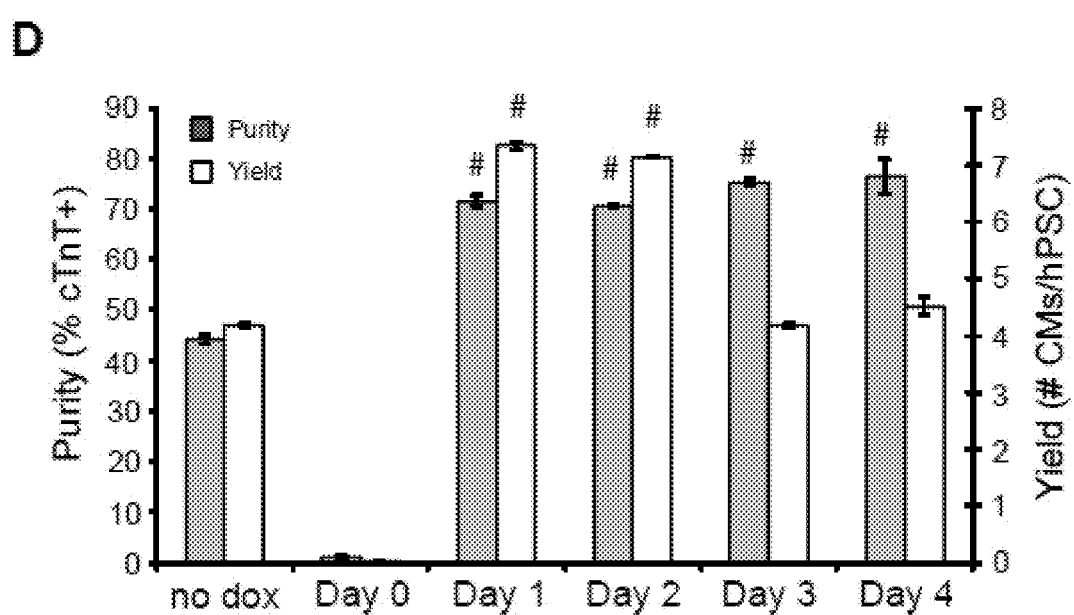

Building on the finding that β-catenin is a key mediator of cardiomyocyte induction by Gsk3 inhibitors, the inventors generated 19-9-11 iPSC lines, ishcat-1 and ishcat-2, expressing two different β-catenin shRNA sequences under control of a Tet-regulated inducible promoter (FIG. 5A). Referring to FIG. 5A, $P_{H1TetO}$ represents the human H1 promoter with Tet operator sequences, red and green sequences are forward and reverse shRNA sequences of β-catenin, and the blue sequence represents the loop sequence. Integration of the lentiviral construct was visualized by mCherry expression and clones were selected based on resistance to puromycin (FIG. 5B). Upon dox (dox) addition, both shRNAs efficiently downregulated β-catenin expression (FIG. 5C). The inventors used these cell lines to examine the stage-specific roles of β-catenin during directed differentiation induced by Activin A and BMP4. Canonical Wnt signaling is essential for cardiac induction, since β-catenin knockdown upon Activin A addition did not generate cTNT-expressing cells in the 19-9-11 ishcat-1 line (FIG. 5D), while the iscramble line showed no response to dox addition (FIG. 4F). Importantly, knockdown of β-catenin expression later in differentiation enhanced cardiogenesis (FIG. 5D). Similar results were observed for 19-9-11 ishcat-2 line (FIG. 4G).

Example 5

Figure 6A:
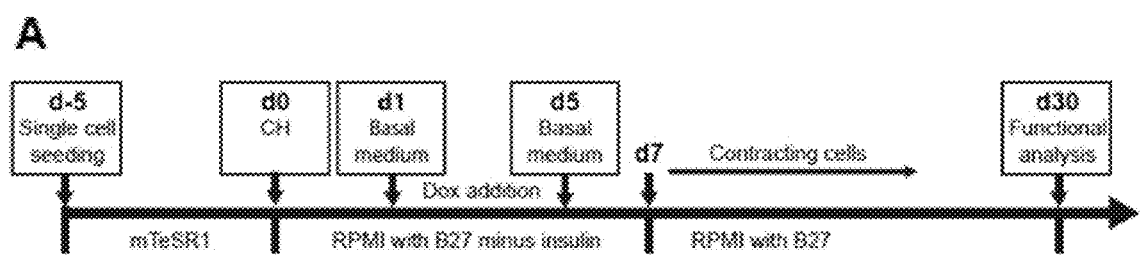
FIGS. 6A-F illustrate that manipulation of Gsk3 and Wnt signaling is sufficient for efficient and reproducible generation of functional cardiomyocytes in the absence of growth factors.
Figure 6B:
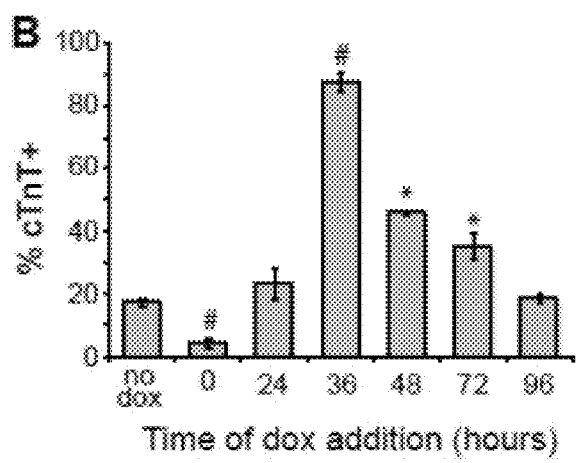
Figure 6C:
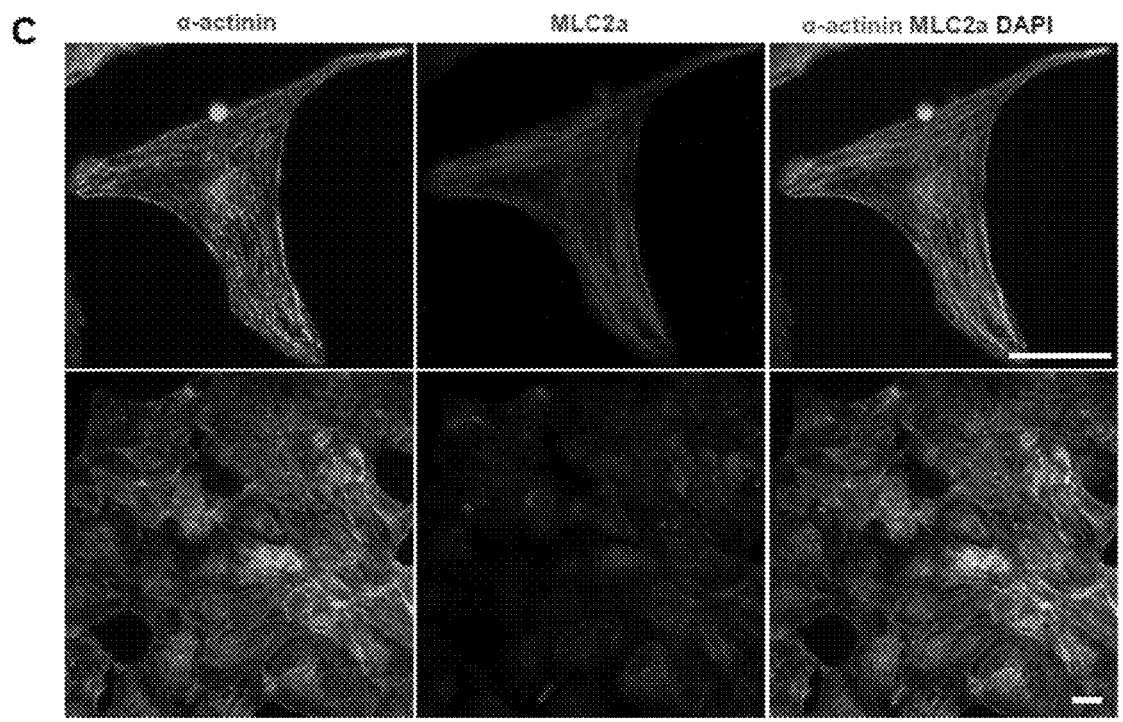
Figure 7A:
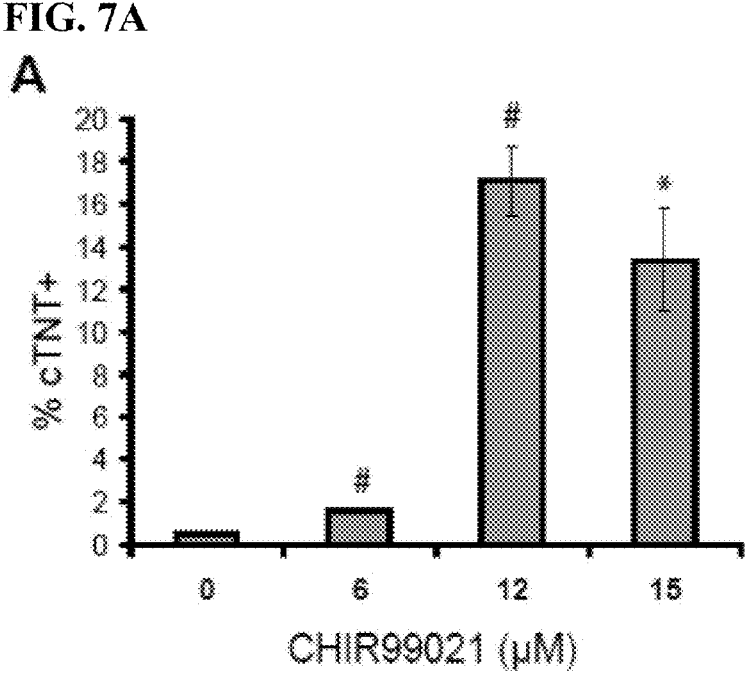
Figure 7B:
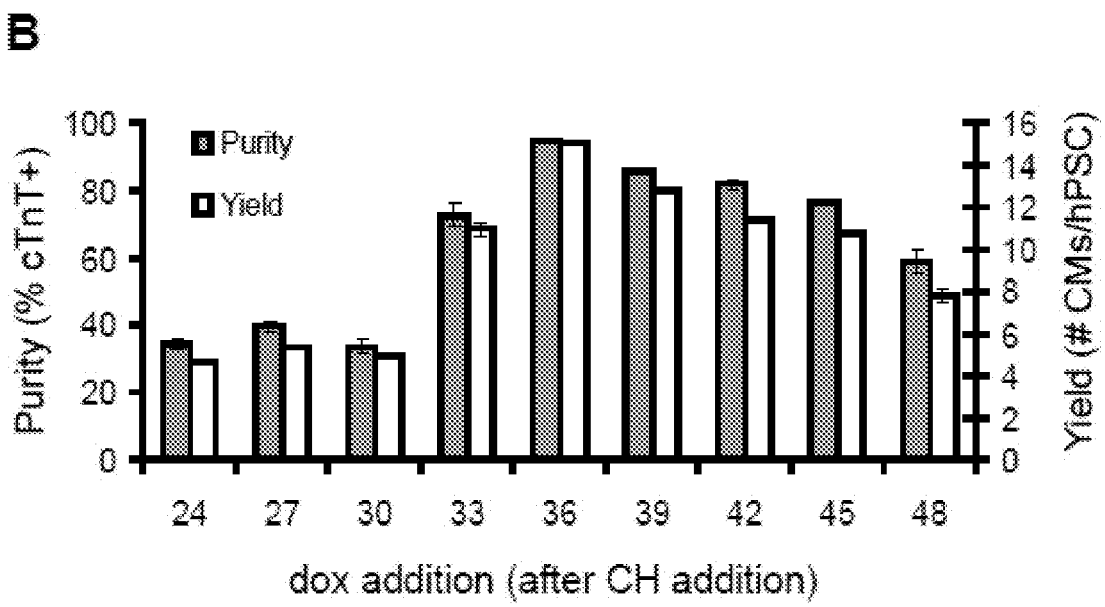

Highly Efficient Generation of Human Cardiomyocytes Solely by Modulating Gsk3 and Wnt Signaling Our results and prior studies (Ren et al., J. Mol. Cell. Cardiol. 51:280-287 (2011); Tran et al., Stem Cells 27:1869-1878 (2009); Wang et al., A.C.S. Chem. Biol. 6, 192-197 (2011); Willems et al., Circ Res. 109:360-364 (2011)) indicate that induction of canonical Wnt signaling early and suppression of canonical Wnt signaling at later stages of differentiation enhance yield of cardiomyocytes. The inventors next sought to determine whether modulating Gsk3 and canonical Wnt signaling alone was sufficient to induce cardiogenesis. Undifferentiated hPS cells were cultured in RPMI/B27-insulin medium containing CH. CH was removed by medium exchange at day 1 and dox was added to the medium at various time points between day 0 and day 4. At day 5, the medium was replaced with RPMI/B27-insulin (FIG. 6A) and cardiomyocyte differentiation was assessed at day 15 by the percentage and yield of cTNT and/or MF20 expressing cells. In the 19-9-11 ishcat-1 line, 12 μM CH produced the most cTNT+ cells at day 15 without additional dox-induced β-catenin knockdown (FIG. 7A). The inventors then investigated the effect of the timing of dox treatment following addition of 12 μM CH. Addition of dox 36 hours following initiation of differentiation generated 95% cTNT+ cells with yields of approximately 15 cTNT+ cells per input iPSC (FIGS. 6B and 7B). A high yield of cTNT+ cells was also obtained using 19-9-11 ishcat-2 and three additional hPS cell lines (IMR90C4, 6-9-9, and H9) transduced with inducible β-catenin shRNA ishcat-1 (FIG. 7C).

Figure 6D:
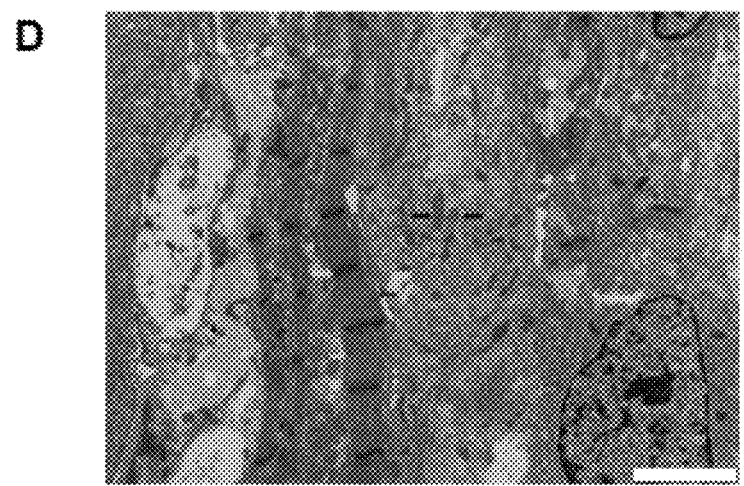
Figure 6E:
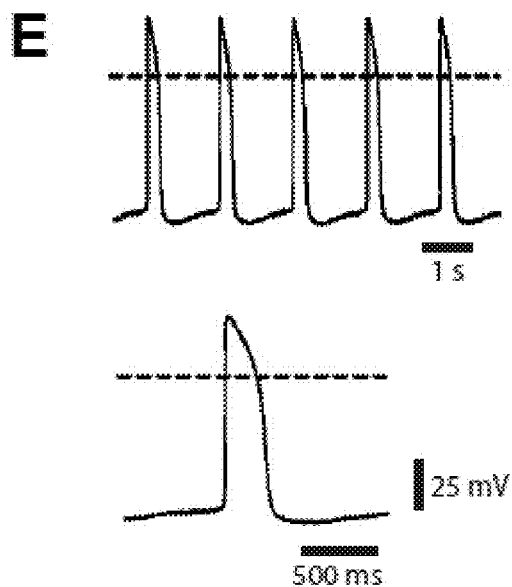
Figure 6F:
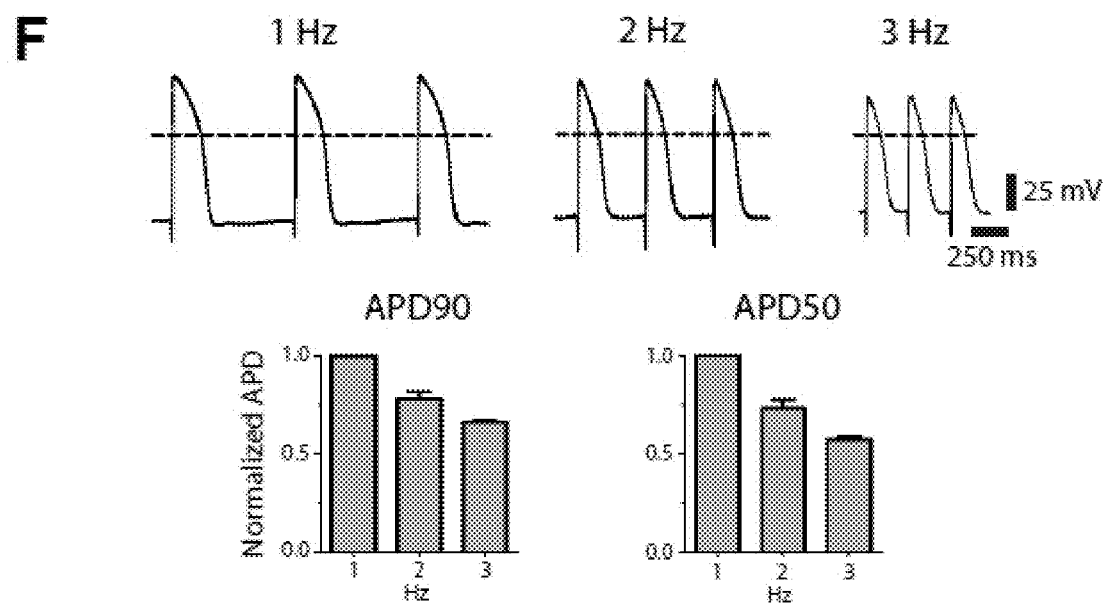
Figure 7H:
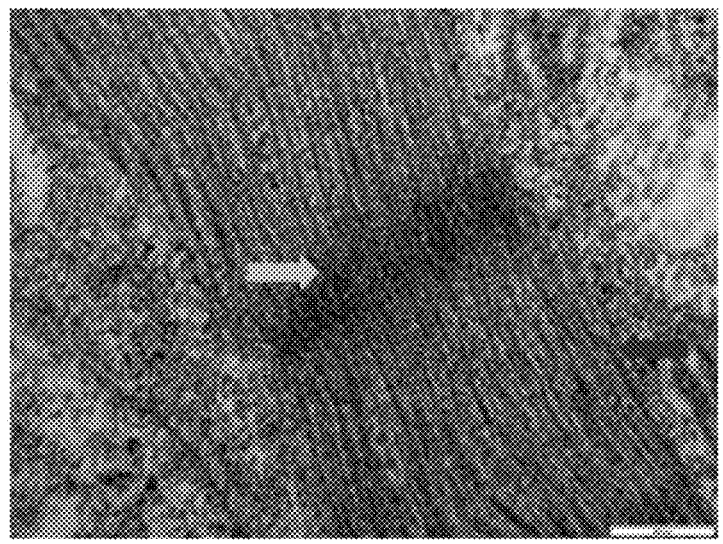
Figure 7I:

The optimal conditions illustrated in FIG. 4B, 12 μM CH followed by dox treatment at 36 hours, yielded relatively pure (>90%) cardiomyocytes that contracted as coordinated sheets in multiple (>50) independent experiments, demonstrating consistency and reproducibility. These cardiomyocytes were maintained as beating cells in culture for more than six months. The cardiomyocytes exhibited normal cardiac sarcomere organization, demonstrated by immunofluorescent staining of α-actinin, MLC2a, and cTnT (FIGS. 6C, 7D, 7E, 7F and 7G). Scanning electron microscopy also identified cells with myofibrillar bundles and transverse Z-bands (FIGS. 4D and 7H), and cells enriched in mitochondria (FIG. 6D). Intercalated disks with desmosomes (FIG. 7I), typical of cardiomyocytes, were also observed. To provide an initial assessment of the functional competence of cardiomyocytes generated by manipulation of canonical Wnt signaling in the absence of growth factors, the inventors performed sharp microelectrode electrophysiological recordings at 29 days post-addition of CH. Representative recordings of action potentials are shown for a ventricular-like cardiomyocytes (FIG. 6E). Cardiomyocytes also exhibited rate adaptation, as evidenced by decreases in action potential duration in response to stimulation at increasing frequencies (FIG. 6F). The observed decreases in duration were comparable in magnitude to those previously observed for hESC- and iPSC-derived cardiomyocytes (He et al., Circ. Res. 93, 32-39 (2003); Zhang et al., Circ. Res. 104: e30-41 (2009)). These results suggest that the ion channels and regulatory proteins involved in action potential generation and regulation are normally expressed in cardiomyocytes generated by Wnt pathway manipulation. Together, these results indicate that functional cardiomyocytes can be successfully generated from hPS cells solely by manipulating canonical Wnt signaling in the absence of exogenous growth factors.

Example 6

Figure 8A:
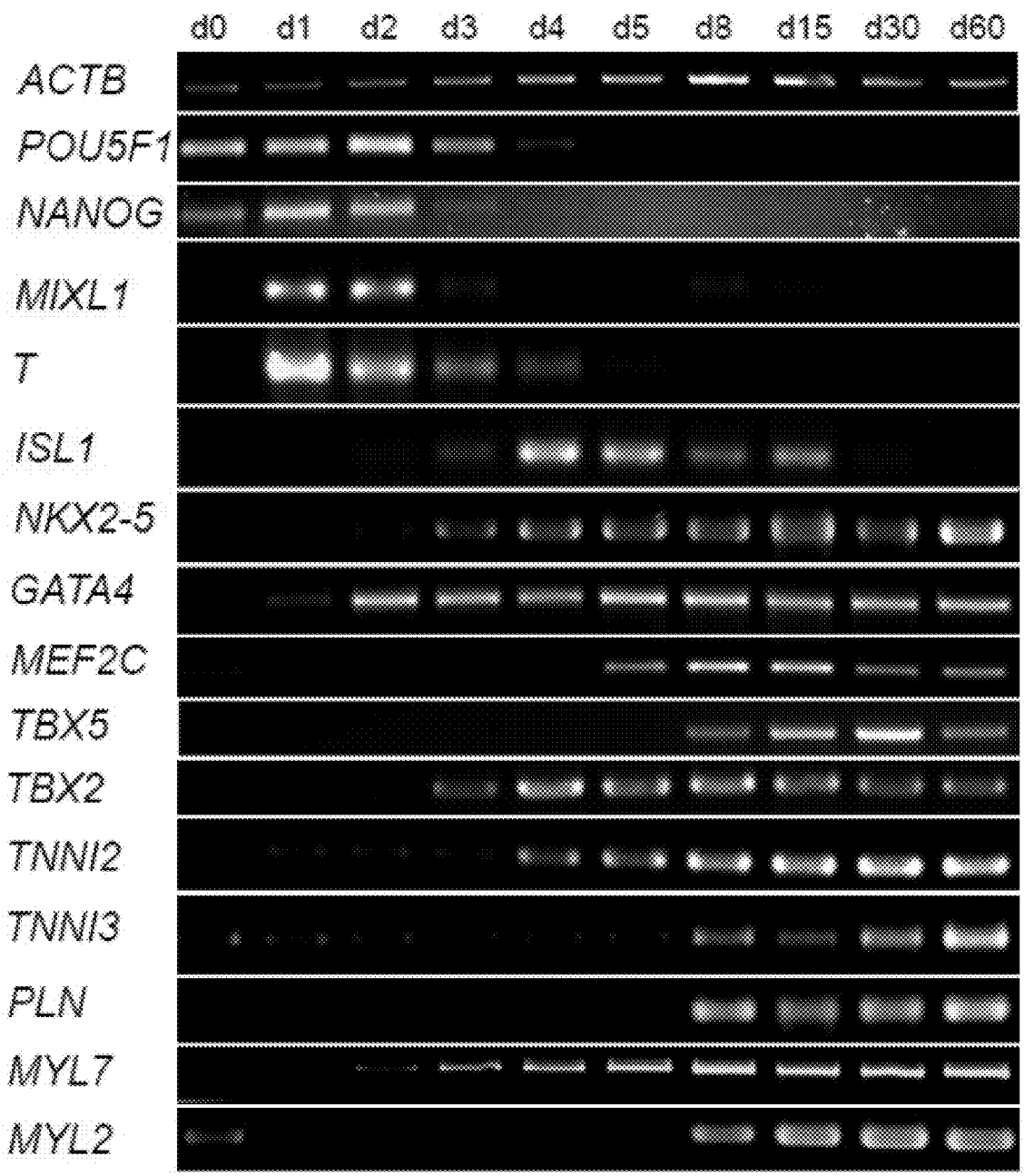
FIGS. 8A-D illustrate molecular characterization of cardiomyocyte generated via Wnt pathway modulation.

Molecular Characterization of Cardiomyocytes Generated by Modulating Gsk3 and Wnt Signaling To better understand the heterogeneity and maturity of cardiomyocytes generated via Wnt pathway manipulation, the inventors examined the expression of genes involved in cardiomyocyte development, myofilament protein expression, and the proliferative capacity of CMs during a period of 60 days post-induction of differentiation. Molecular analysis revealed dynamic changes in gene expression with the induction of the primitive-streak-like genes T (Asashima et al., FASEB J. 23:114-122 (2009)) and MIXL1 (Davis et al., Blood 111:1876-1884 (2008)) shortly after CH addition, and downregulation of pluripotency markers OCT4 and NANOG within 4 days (FIG. 8A). Expression of the cardiac transcription factor NKX2.5 (Lints et al., Development 119: 969 (1993)) began at day 3 and persisted throughout the 60 day experiment. ISL1, a gene that marks progenitors of the secondary heart field in the early embryo (Bu et al., Nature 460:113-117 (2009)), was also detected at day 3, but ceased by day 30. TBX5 (Bruneau et al., Dev. Biol. 211:100-108 (1999)), GATA4 (Kuo et al., Gene Dev. 11:1048-1060 (1997a); Kuo et al., Circulation 96:1686-1686 (1997b)), and MEF2C (Edmondson et al., Development 120:1251-1263 (1994)) are important regulators of cardiomyocyte development and their expression has been used to directly convert fibroblasts into cardiomyocytes (Ieda et al., Cell 142:375-386 (2010)). These three genes were expressed at different time points following β-catenin knockdown (at 36 hr) and expression of these genes persisted for the full 60 days of the experiment (FIG. 8A).

Figure 8B:
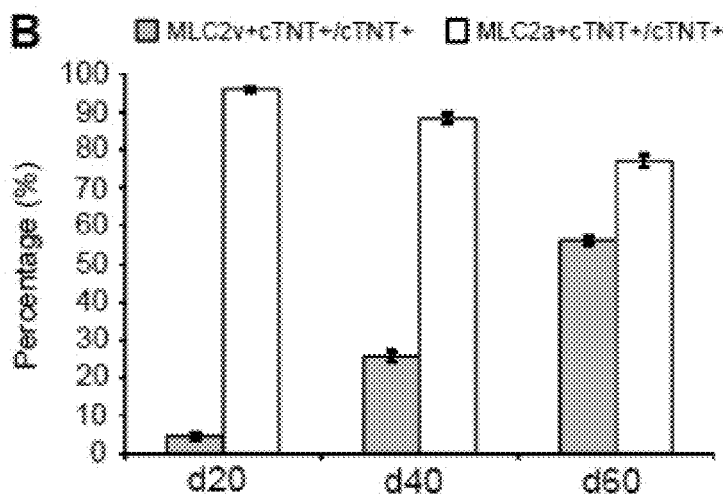
Figure 8C:
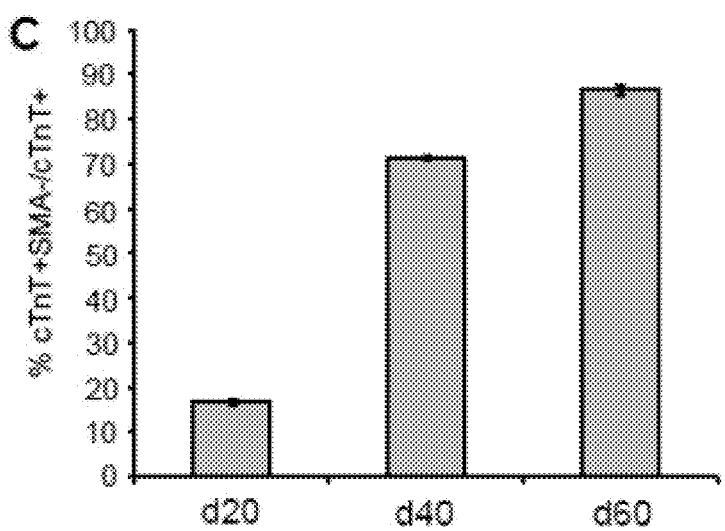
Figure 8D:
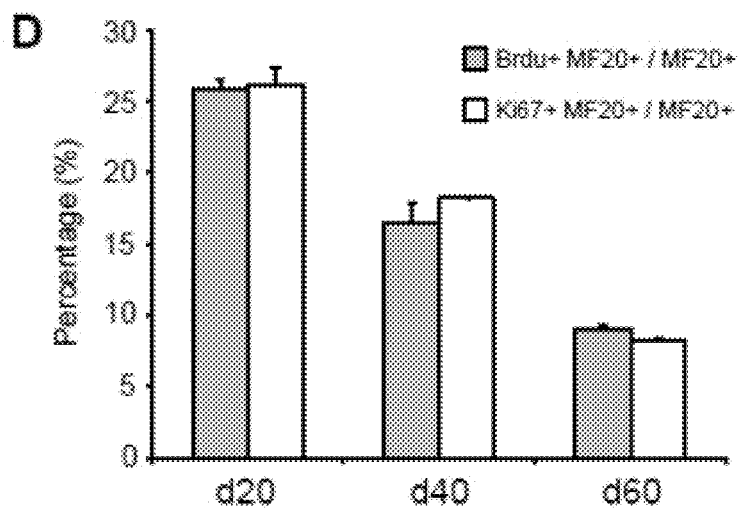

To quantitatively monitor the differential expression of myofilament proteins involved in cardiomyocyte specification, the inventors profiled MLC2a and MLC2v expression 20, 40, and 60 days following induction of differentiation. At day 20, very few cTnT+ cells contained detectable levels of MLC2v, a marker of mature ventricular cardiomyocytes (Franco et al., Anat. Rec. 254:135-146 (1999); Kubalak et al., J. Biol. Chem. 269:16961-16970 (1994); Segev et al., Dev. Growth Differ. 47:295-306 (2005)), while virtually all cTnT+ cells contained MLC2a, which is expressed in mature atrial and immature ventricular cardiomyocytes (Kubalak et al., J. Biol. Chem. 269:16961-16970 (1994)) (FIG. 8B). By day 60, greater than 50% of the cTnT+ cells expressed MLC2v while the percentage of cTnT+ cells expressing MLC2a decreased to less than 80%, suggesting maturation of a population of ventricular cardiomyocytes. Smooth muscle actin (SMA) is expressed in the earliest embryonic cardiomyocytes but not in more mature cardiomyocytes (Matsui et al., Dev. Dynam. 233:1419-1429 (2005); Nakajima et al., Develop. Biol. 245:291-303 (2002); Ruzicka and Schwartz, J. Cell Biol. 107:2575-2586 (1988); Sugi and Lough, Dev. Dyn. 193:116-124 (1992)). At day 20, greater than 80% of cTnT+ cells also expressed SMA, but by day 60 less than 15% of the CMs were SMA+(FIG. 8C). Another hallmark of CM maturation is the loss of proliferative capacity. To assess cell proliferation, the inventors quantified Ki67 staining and BrdU incorporation in MF20+ cells generated by the protocol illustrated in FIG. 6A. The percentage of proliferating cardiomyocytes decreased from about 25% at day 20 to less than 10% at day 60 (FIG. 8D). Taken together, these results indicate cardiomyocytes generated by WNT pathway modulation transition from an early phenotype to a more mature state during culture.

Example 7

Induction of TGFβ Superfamily Signaling by Gsk3 Inhibitors

Figure 9A:
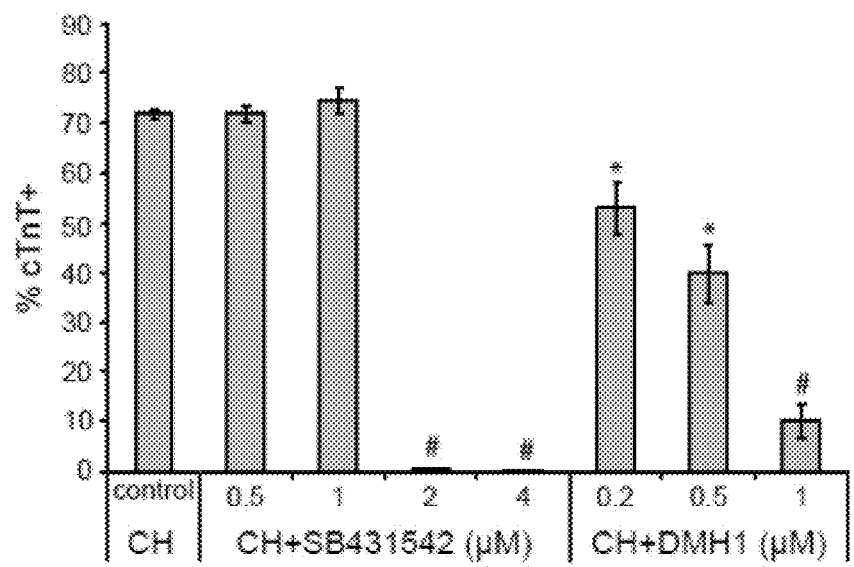
FIGS. 9A-C illustrate induction of TGFβ superfamily signaling by GSK3 inhibitor treatment.
Figure 9B:
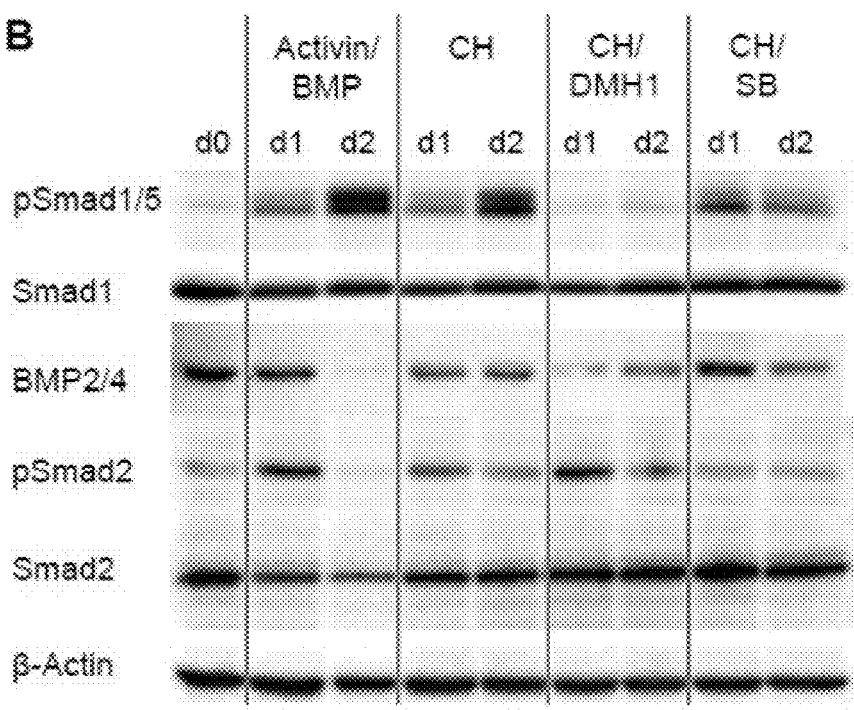
Figure 9C:
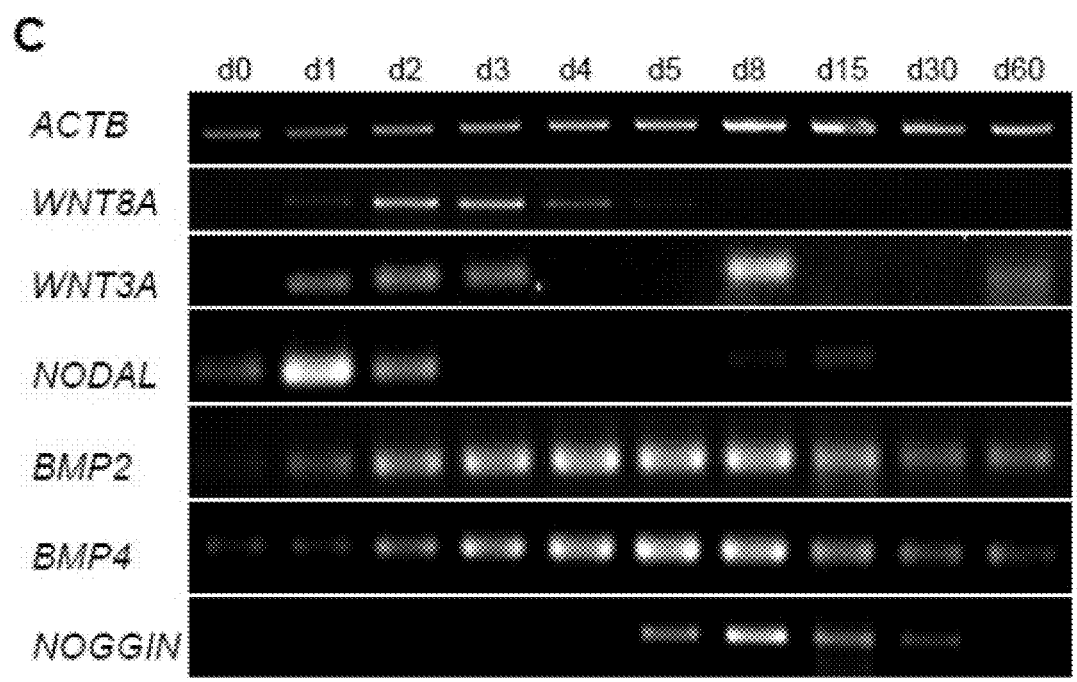
Figure 10A:
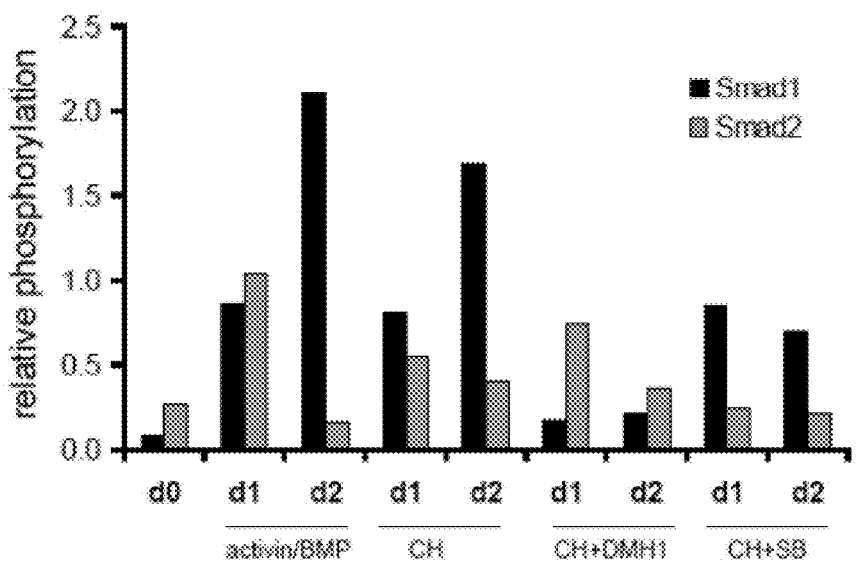
FIGS. 10A-C illustrate protein expression patterns in differentiated cardiomyocytes.

To determine whether canonical Wnt signaling requires TGFβ superfamily signaling to induce cardiogenesis, the inventors quantified cTnT+ cell generation in 19-9-11 ishcat-2 cells when Activin A and BMP4 signaling antagonists were presented during the first 24 hr of cardiomyocyte induction with 12 μM CH. All samples were treated with dox at 48 hours. SB431542 (SB), an inhibitor of the Activin A receptor-like kinase ALK5 (Inman et al., Mol. Pharmacol. 62:65-74 (2002)), completely blocked cardiomyocyte specification at concentrations greater than 2 μM (FIG. 9A). Addition of DMH1, which inhibits the BMP ALK2 receptor (Hao et al., A.C.S. Chem. Biol. 5:245-253 (2010)), also decreased the percentage of cTnT+ cells in a concentration-dependent manner (FIG. 9A). To further investigate the role of TGFβ superfamily signaling in Wnt pathway-mediated cardiogenesis the inventors assessed Smad1/5 and Smad2 phosphorylation, downstream of BMP4 and Activin A signaling respectively. As expected, substantial Smad1/5 and Smad2 phosphorylation was detected in cells that had been treated with Activin A and BMP4 (FIGS. 9B and 10A). CH treatment resulted in Smad1/5 and Smad2 activation at levels comparable to those induced by Activin A and BMP4. Smad1/5 phosphorylation was strongly attenuated by DMH1 while SB diminished Smad2 phosphorylation. Interestingly, endogenous BMP2/4 was detected in undifferentiated hPS cells and cells following CH treatment (FIGS. 9B and 10A). Gene expression analysis revealed that BMP2 and BMP4 were gradually upregulated upon CH treatment and persisted throughout the differentiation process while a transient upregulation upon CH treatment was observed for NODAL expression (FIG. 9C). These results indicate that Activin/Nodal and BMP signaling are necessary for cardiogenesis induced via Wnt pathway regulators and suggests that this signaling may result from endogenous Nodal and BMPs produced during differentiation.

Example 8

Figure 10B:
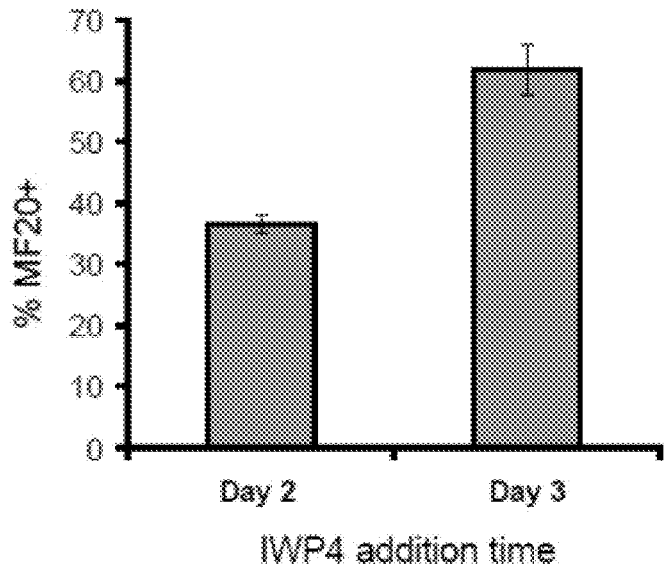
Figure 10C:
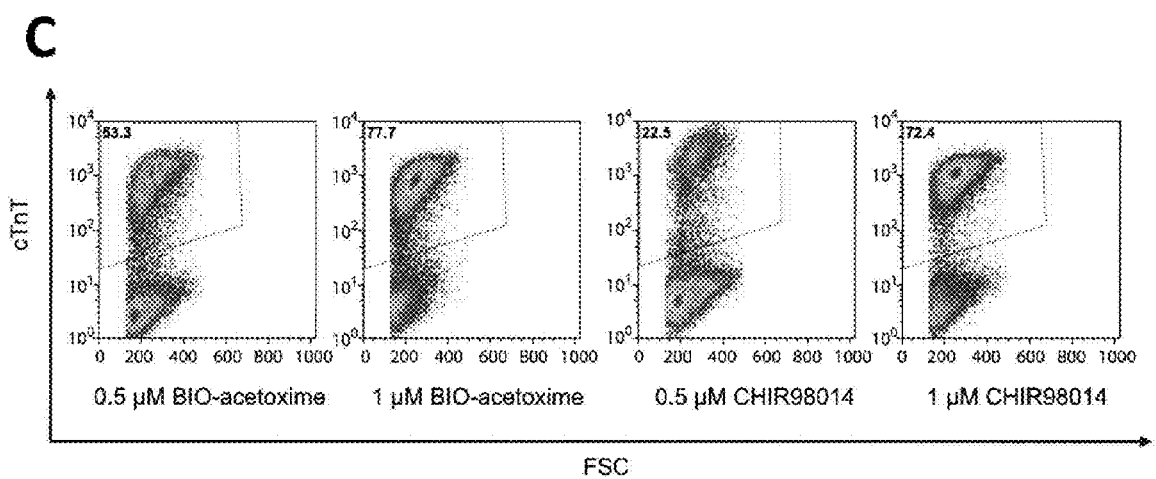
Figure 11A:
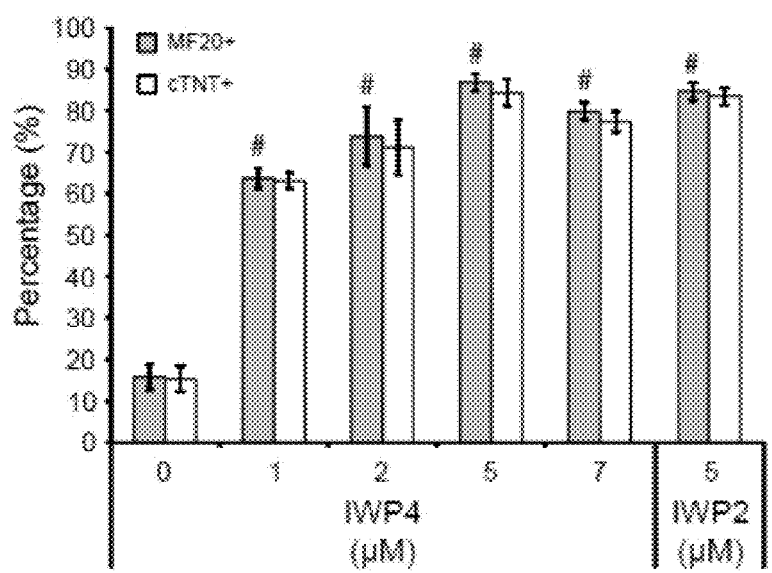
FIGS. 11A-B illustrate development of a protocol for differentiation of hPS cells to cardiomyocytes in fully defined conditions via small molecule modulation of Gsk3 and Wnt signaling.
Figure 11B:
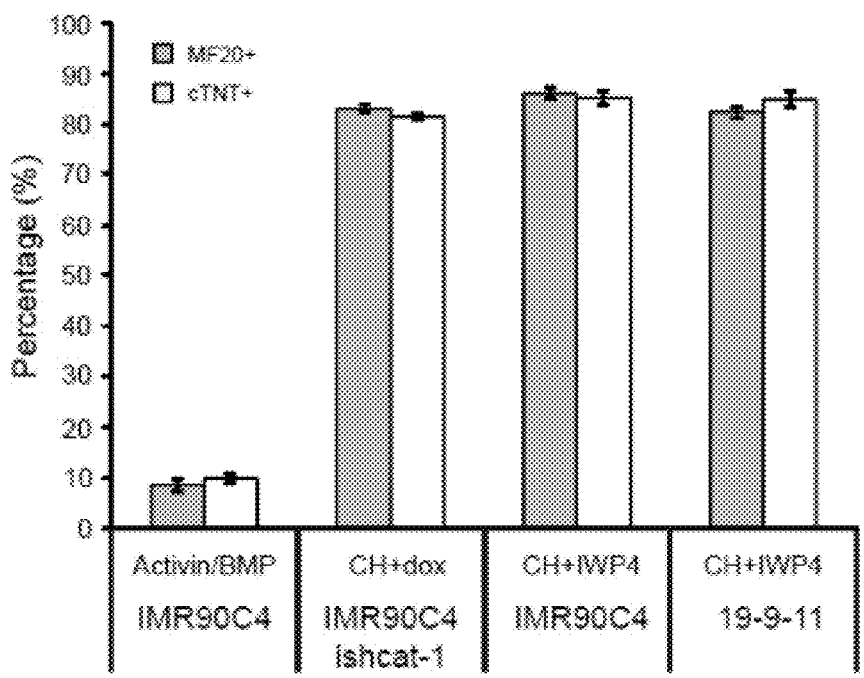

Differentiation of hPS Cells to Cardiomyocytes in Fully Defined Conditions Via Small Molecule Modulation of Gsk3 and Wnt Signaling While shRNA inhibition of β-catenin provides specific and facile temporal regulation of canonical Wnt signaling, this method requires genetic modification of the hPS cell line which limits its potential clinical utility. The inventors next used the mechanistic insight these modified lines provided regarding the sufficiency of canonical Wnt signaling in cardiomyogenesis to develop a completely defined, growth factor free method of efficiently generating cardiomyocytes from unmodified hPS cell lines using small molecules. First, 19-9-11 iPSCs were maintained in mTeSR1 on Matrigel® for five days, and then the medium was switched to RPMI/B27-insulin containing 12 μM CH. IWP4 and IWP2, which prevent palmitylation of Wnt proteins by porcupine thereby blocking Wnt protein secretion and activity (Chen et al., Nat. Chem. Biol. 5:100-107 (2009)), were used to inhibit Wnt signaling. Addition of 5 μM IWP4 at day 3 resulted in optimal generation of cardiomyocytes (FIGS. 11A and 10B). Similar to results obtained with the 19-9-11 ishcat-1 cell line, CH treatment of 19-9-11 cells alone only generated 16% cTNT+ or MF20+ cells after 15 days, while adding 5 μM IWP4 or IWP2 at day 3 increased this to 87% cTNT+ or MF20+ cells. Similar results were obtained when CH was replaced with other GSK3 inhibitors, including CHIR98014, and BIO-acetoxime (FIG. 10C). In order to achieve fully defined culture conditions, Matrigel® was replaced with a defined peptide acrylate surface (Synthemax) during both hPS cell expansion and differentiation. 19-9-11 and IMR90C4 iPSCs plated on Synthemax plates and treated with CH and IWP4 also generated approximately 85% cTNT+ or MF20+ cells, comparable to the efficiency of differentiation observed after CH treatment followed by expression of β-catenin shRNA (FIG. 11B). Thus, optimization of canonical WNT signaling via stage-specific addition of small molecule agonists and antagonists produces high yields of functional cardiomyocytes in a completely defined, growth factor free culture system.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method for generating a cell population of human cardiomyocyte progenitors, comprising inhibiting Wnt/β-catenin signaling in a first cell population to obtain a second cell population comprising human cardiomyocyte progenitors, wherein inhibiting comprises culturing the first cell population in the presence of an inhibitor of Wnt/β-catenin signaling, wherein the culturing is substantially free of exogenous growth factors, and wherein the first cell population is obtained by activating Wnt/β-catenin signaling in human pluripotent stem cells by culturing the human pluripotent stem cells in the presence of a Gsk3 inhibitor.

2. The method of claim 1, wherein the first cell population comprises cells that overexpress β-catenin.

3. The method of claim 2, wherein β-catenin overexpression is inducible.

4. The method of claim 1, wherein the Gsk3 inhibitor is a small molecule selected from the group consisting of CHIR 99021, CHIR 98014, BIO-acetoxime, BIO, LiCl, SB 216763, SB 415286, AR A014418, 1-Azakenpaullone, and Bis-7-indolylmaleimide, or a combination thereof.

5. The method of claim 1, wherein the Gsk3 inhibitor comprises a Gsk3-targeting short interfering RNA (siRNA) polynucleotide.

6. The method of claim 5, wherein the Gsk3-targeting siRNA is inducible.

7. The method of claim 1, wherein the inhibitor of Gsk3 is a dominant negative form of Gsk3.

8. The method of claim 1, wherein the step of inhibiting Wnt/β-catenin signaling comprises culturing the first cell population in the presence of a small molecule that inhibits Wnt/β-catenin signaling.

9. The method of claim 8, wherein the small molecule that inhibits Wnt/β-catenin signaling is selected from the group consisting of XAV939, IWR-1, IWR-2, IWR-3, IWR-4, IWR-5, IWP-1, IWP-2, IWP-3, and IWP-4.

10. The method of claim 9, wherein the small molecule that inhibits Wnt/β-catenin signaling is XAV939.

11. The method of claim 8, wherein the small molecule prevents palmitoylation of Wnt proteins by Porcupine (Porcn).

12. The method of claim 11, wherein the small molecule that prevents palmitoylation of Wnt proteins by Porcn is selected from the group consisting of IWP-2 and IWP-4.

13. The method of claim 1, wherein the step of inhibiting Wnt/β-catenin signaling comprises contacting the first cell population with at least one antibody that blocks activation of a Wnt ligand receptor.

14. The method of claim 13, wherein the at least one antibody binds to one or more Wnt ligand family members.

15. The method of claim 1, wherein the step of inhibiting Wnt/β-catenin signaling comprises reducing β-catenin expression in the first cell population.

16. The method of claim 15, wherein reducing β-catenin expression comprises expressing a β-catenin-targeting short hairpin RNA (shRNA) in the first cell population.

17. The method of claim 16, wherein the β-catenin-targeting shRNA is inducible.

18. The method of claim 1, wherein at least one of the first cell population and the second population is cultured under conditions free of exogenous growth factors.

19. The method of claim 1, further comprising culturing the second cell population in the substantial absence of exogenous growth factors after ending the inhibition of Wnt/β-catenin signaling to obtain a cell population comprising cardiomyocytes.

20. The method of claim 19, wherein the culturing comprises culturing in a medium comprising RPMI base medium, wherein at least 70% of the cells in the cell population comprising cardiomyocytes are cardiac troponin-T (cTnT)-positive.

21. The method of claim 20, wherein the cell population comprising at least 70% cTnT-positive cells is obtained without a cell separation or selection step.

* * * * *

SEQUENCE LISTING

```
<160> NUMBER OF SEQ ID NOS: 64

<210> SEQ ID NO 1
<211> LENGTH: 19
<212> TYPE: DNA
<213> ORGANISM: Artificial Sequence
<220> FEATURE:
<223> OTHER INFORMATION: OCT4 forward primer

<400> SEQUENCE: 1
cagtgcccga aacccacac                                                19

<210> SEQ ID NO 2
<211> LENGTH: 20
```

<210> SEQ ID NO 2
<211> LENGTH: 20
<212> TYPE: DNA
<213> ORGANISM: Artificial Sequence
<220> FEATURE:
<223> OTHER INFORMATION: OCT4 reverse primer

<400> SEQUENCE: 2
ggagacccag cagcctcaaa                                           20

<210> SEQ ID NO 3
<211> LENGTH: 23
<212> TYPE: DNA
<213> ORGANISM: Artificial Sequence
<220> FEATURE:
<223> OTHER INFORMATION: NANOG forward primer

<400> SEQUENCE: 3
cgaagaatag caatggtgtg acg                                       23

<210> SEQ ID NO 4
<211> LENGTH: 21
<212> TYPE: DNA
<213> ORGANISM: Artificial Sequence
<220> FEATURE:
<223> OTHER INFORMATION: NANOG reverse primer

<400> SEQUENCE: 4
ttccaaagca gcctccaagt c                                         21

<210> SEQ ID NO 5
<211> LENGTH: 20
<212> TYPE: DNA
<213> ORGANISM: Artificial Sequence
<220> FEATURE:
<223> OTHER INFORMATION: SOX2 forward primer

<400> SEQUENCE: 5
caagatgcac aactcggaga                                           20

<210> SEQ ID NO 6
<211> LENGTH: 20
<212> TYPE: DNA
<213> ORGANISM: Artificial Sequence
<220> FEATURE:
<223> OTHER INFORMATION: SOX2 reverse primer

<400> SEQUENCE: 6
gttcatgtgc gcgtaactgt                                           20

<210> SEQ ID NO 7
<211> LENGTH: 23
<212> TYPE: DNA
<213> ORGANISM: Artificial Sequence
<220> FEATURE:
<223> OTHER INFORMATION: CTNNB1 forward primer

<400> SEQUENCE: 7
gaatgagact gctgatcttg gac                                       23

<210> SEQ ID NO 8
<211> LENGTH: 20
<212> TYPE: DNA
<213> ORGANISM: Artificial Sequence
<220> FEATURE:
<223> OTHER INFORMATION: CTNNB1 reverse primer

<400> SEQUENCE: 8
ctgattgctg tcacctggag                                              20

<210> SEQ ID NO 9
<211> LENGTH: 22
<212> TYPE: DNA
<213> ORGANISM: Artificial Sequence
<220> FEATURE:
<223> OTHER INFORMATION: GSC forward primer

<400> SEQUENCE: 9
cgaggagaaa gtggaggtct gg                                           22

<210> SEQ ID NO 10
<211> LENGTH: 19
<212> TYPE: DNA
<213> ORGANISM: Artificial Sequence
<220> FEATURE:
<223> OTHER INFORMATION: GSC reverse primer

<400> SEQUENCE: 10
gcagcgcgtg tgcaagaaa                                               19

<210> SEQ ID NO 11
<211> LENGTH: 20
<212> TYPE: DNA
<213> ORGANISM: Artificial Sequence
<220> FEATURE:
<223> OTHER INFORMATION: MIXL1 forward primer

<400> SEQUENCE: 11
cagagtggga aatccttcca                                              20

<210> SEQ ID NO 12
<211> LENGTH: 20
<212> TYPE: DNA
<213> ORGANISM: Artificial Sequence
<220> FEATURE:
<223> OTHER INFORMATION: MIXL1 reverse primer

<400> SEQUENCE: 12
tgagtccagc tttgaaccaa                                              20

<210> SEQ ID NO 13
<211> LENGTH: 20
<212> TYPE: DNA
<213> ORGANISM: Artificial Sequence
<220> FEATURE:
<223> OTHER INFORMATION: T forward primer

<400> SEQUENCE: 13
cttccctgag acccagttca                                              20

<210> SEQ ID NO 14
<211> LENGTH: 20
<212> TYPE: DNA
<213> ORGANISM: Artificial Sequence
<220> FEATURE:
<223> OTHER INFORMATION: T reverse primer

<400> SEQUENCE: 14
cagggttggg tacctgtcac                                              20

<210> SEQ ID NO 15
<211> LENGTH: 21
<212> TYPE: DNA
<213> ORGANISM: Artificial Sequence

```
<220> FEATURE:
<223> OTHER INFORMATION: MSX1 forward primer

<400> SEQUENCE: 15
ccgagaggac cccgtggatg c                                              21

<210> SEQ ID NO 16
<211> LENGTH: 21
<212> TYPE: DNA
<213> ORGANISM: Artificial Sequence
<220> FEATURE:
<223> OTHER INFORMATION: MSX1 reverse primer

<400> SEQUENCE: 16
gcctcttgta gtctctttgc c                                              21

<210> SEQ ID NO 17
<211> LENGTH: 18
<212> TYPE: DNA
<213> ORGANISM: Artificial Sequence
<220> FEATURE:
<223> OTHER INFORMATION: ISL1 forward primer

<400> SEQUENCE: 17
cacaagcgtc tcgggatt                                                  18

<210> SEQ ID NO 18
<211> LENGTH: 19
<212> TYPE: DNA
<213> ORGANISM: Artificial Sequence
<220> FEATURE:
<223> OTHER INFORMATION: ISL1 reverse primer

<400> SEQUENCE: 18
agtggcaagt cttccgaca                                                 19

<210> SEQ ID NO 19
<211> LENGTH: 19
<212> TYPE: DNA
<213> ORGANISM: Artificial Sequence
<220> FEATURE:
<223> OTHER INFORMATION: WNT3A forward primer

<400> SEQUENCE: 19
gccccactcg gatacttct                                                 19

<210> SEQ ID NO 20
<211> LENGTH: 19
<212> TYPE: DNA
<213> ORGANISM: Artificial Sequence
<220> FEATURE:
<223> OTHER INFORMATION: WNT3A reverse primer

<400> SEQUENCE: 20
ggcatgatct ccacgtagt                                                 19

<210> SEQ ID NO 21
<211> LENGTH: 20
<212> TYPE: DNA
<213> ORGANISM: Artificial Sequence
<220> FEATURE:
<223> OTHER INFORMATION: WNT8A forward primer

<400> SEQUENCE: 21
acaggtccca aggcctatct                                                20
```

<210> SEQ ID NO 22
<211> LENGTH: 20
<212> TYPE: DNA
<213> ORGANISM: Artificial Sequence
<220> FEATURE:
<223> OTHER INFORMATION: WNT8A reverse primer

<400> SEQUENCE: 22
atcctttccc caaattccac                                              20

<210> SEQ ID NO 23
<211> LENGTH: 24
<212> TYPE: DNA
<213> ORGANISM: Artificial Sequence
<220> FEATURE:
<223> OTHER INFORMATION: NKX2-5 forward primer

<400> SEQUENCE: 23
gcgattatgc agcgtgcaat gagt                                         24

<210> SEQ ID NO 24
<211> LENGTH: 24
<212> TYPE: DNA
<213> ORGANISM: Artificial Sequence
<220> FEATURE:
<223> OTHER INFORMATION: NKX2-5 reverse primer

<400> SEQUENCE: 24
aacataaata cgggtgggtg cgtg                                         24

<210> SEQ ID NO 25
<211> LENGTH: 20
<212> TYPE: DNA
<213> ORGANISM: Artificial Sequence
<220> FEATURE:
<223> OTHER INFORMATION: GATA4 forward primer

<400> SEQUENCE: 25
tccaaaccag aaaacggaag                                              20

<210> SEQ ID NO 26
<211> LENGTH: 20
<212> TYPE: DNA
<213> ORGANISM: Artificial Sequence
<220> FEATURE:
<223> OTHER INFORMATION: GATA4 reverse primer

<400> SEQUENCE: 26
aagaccaggc tgttccaaga                                              20

<210> SEQ ID NO 27
<211> LENGTH: 20
<212> TYPE: DNA
<213> ORGANISM: Artificial Sequence
<220> FEATURE:
<223> OTHER INFORMATION: MEF2C forward primer

<400> SEQUENCE: 27
agccctgagt ctgaggacaa                                              20

<210> SEQ ID NO 28
<211> LENGTH: 20
<212> TYPE: DNA
<213> ORGANISM: Artificial Sequence
<220> FEATURE:
<223> OTHER INFORMATION: MEF2C reverse primer

```
<400> SEQUENCE: 28
gtgagccagt ggcaataggt                                                     20

<210> SEQ ID NO 29
<211> LENGTH: 20
<212> TYPE: DNA
<213> ORGANISM: Artificial Sequence
<220> FEATURE:
<223> OTHER INFORMATION: TBX5 forward primer

<400> SEQUENCE: 29
gaaacccagc ataggagctg                                                     20

<210> SEQ ID NO 30
<211> LENGTH: 21
<212> TYPE: DNA
<213> ORGANISM: Artificial Sequence
<220> FEATURE:
<223> OTHER INFORMATION: TBX5 reverse primer

<400> SEQUENCE: 30
cagcctcaca tcttaccctg t                                                   21

<210> SEQ ID NO 31
<211> LENGTH: 20
<212> TYPE: DNA
<213> ORGANISM: Artificial Sequence
<220> FEATURE:
<223> OTHER INFORMATION: TBX2 forward primer

<400> SEQUENCE: 31
agtggatggc taagcctgtg                                                     20

<210> SEQ ID NO 32
<211> LENGTH: 20
<212> TYPE: DNA
<213> ORGANISM: Artificial Sequence
<220> FEATURE:
<223> OTHER INFORMATION: TBX2 reverse primer

<400> SEQUENCE: 32
acgggttgtt gtcgatcttc                                                     20

<210> SEQ ID NO 33
<211> LENGTH: 20
<212> TYPE: DNA
<213> ORGANISM: Artificial Sequence
<220> FEATURE:
<223> OTHER INFORMATION: TNNI3 forward primer

<400> SEQUENCE: 33
ctgcagattg caaagcaaga                                                     20

<210> SEQ ID NO 34
<211> LENGTH: 20
<212> TYPE: DNA
<213> ORGANISM: Artificial Sequence
<220> FEATURE:
<223> OTHER INFORMATION: TNNI3 reverse primer

<400> SEQUENCE: 34
cctccttctt cacctgcttg                                                     20

<210> SEQ ID NO 35
```

-continued

<210> SEQ ID NO 35
<211> LENGTH: 24
<212> TYPE: DNA
<213> ORGANISM: Artificial Sequence
<220> FEATURE:
<223> OTHER INFORMATION: TNNT2 forward primer

<400> SEQUENCE: 35
ttcaccaaag atctgctcct cgct                                          24

<210> SEQ ID NO 36
<211> LENGTH: 26
<212> TYPE: DNA
<213> ORGANISM: Artificial Sequence
<220> FEATURE:
<223> OTHER INFORMATION: TNNT2 reverse primer

<400> SEQUENCE: 36
ttattactgg tgtggagtgg gtgtgg                                        26

<210> SEQ ID NO 37
<211> LENGTH: 21
<212> TYPE: DNA
<213> ORGANISM: Artificial Sequence
<220> FEATURE:
<223> OTHER INFORMATION: MYL7 forward primer

<400> SEQUENCE: 37
gaggagaatg gccagcagga a                                             21

<210> SEQ ID NO 38
<211> LENGTH: 21
<212> TYPE: DNA
<213> ORGANISM: Artificial Sequence
<220> FEATURE:
<223> OTHER INFORMATION: MYL7 reverse primer

<400> SEQUENCE: 38
gcgaacatct gctccacctc a                                             21

<210> SEQ ID NO 39
<211> LENGTH: 24
<212> TYPE: DNA
<213> ORGANISM: Artificial Sequence
<220> FEATURE:
<223> OTHER INFORMATION: MYL2 forward primer

<400> SEQUENCE: 39
acatcatcac ccacggagaa gaga                                          24

<210> SEQ ID NO 40
<211> LENGTH: 24
<212> TYPE: DNA
<213> ORGANISM: Artificial Sequence
<220> FEATURE:
<223> OTHER INFORMATION: MYL2 reverse primer

<400> SEQUENCE: 40
attggaacat ggcctctgga tgga                                          24

<210> SEQ ID NO 41
<211> LENGTH: 20
<212> TYPE: DNA
<213> ORGANISM: Artificial Sequence
<220> FEATURE:
<223> OTHER INFORMATION: PLN forward primer

<400> SEQUENCE: 41
acagctgcca aggctaccta                                        20

<210> SEQ ID NO 42
<211> LENGTH: 20
<212> TYPE: DNA
<213> ORGANISM: Artificial Sequence
<220> FEATURE:
<223> OTHER INFORMATION: PLN reverse primer

<400> SEQUENCE: 42
gcttttgacg tgcttgttga                                        20

<210> SEQ ID NO 43
<211> LENGTH: 20
<212> TYPE: DNA
<213> ORGANISM: Artificial Sequence
<220> FEATURE:
<223> OTHER INFORMATION: CD31 forward primer

<400> SEQUENCE: 43 gctgacccتt ctgctctgtt                                        20

<210> SEQ ID NO 44
<211> LENGTH: 20
<212> TYPE: DNA
<213> ORGANISM: Artificial Sequence
<220> FEATURE:
<223> OTHER INFORMATION: CD31 reverse primer

<400> SEQUENCE: 44
tgagaggtgg tgctgacatc                                        20

<210> SEQ ID NO 45
<211> LENGTH: 20
<212> TYPE: DNA
<213> ORGANISM: Artificial Sequence
<220> FEATURE:
<223> OTHER INFORMATION: NODAL forward primer

<400> SEQUENCE: 45
cttcctgagc caacaagagg                                        20

<210> SEQ ID NO 46
<211> LENGTH: 20
<212> TYPE: DNA
<213> ORGANISM: Artificial Sequence
<220> FEATURE:
<223> OTHER INFORMATION: NODAL reverse primer

<400> SEQUENCE: 46
aggtgacctg ggacaaagtg                                        20

<210> SEQ ID NO 47
<211> LENGTH: 20
<212> TYPE: DNA
<213> ORGANISM: Artificial Sequence
<220> FEATURE:
<223> OTHER INFORMATION: BMP2 forward primer

<400> SEQUENCE: 47
tcaagccaaa cacaaacagc                                        20

<210> SEQ ID NO 48
<211> LENGTH: 20
<212> TYPE: DNA

```
<213> ORGANISM: Artificial Sequence
<220> FEATURE:
<223> OTHER INFORMATION: BMP2 reverse primer

<400> SEQUENCE: 48
acgtctgaac aatggcatga                                              20

<210> SEQ ID NO 49
<211> LENGTH: 20
<212> TYPE: DNA
<213> ORGANISM: Artificial Sequence
<220> FEATURE:
<223> OTHER INFORMATION: BMP4 forward primer

<400> SEQUENCE: 49
tgagcctttc cagcaagttt                                              20

<210> SEQ ID NO 50
<211> LENGTH: 20
<212> TYPE: DNA
<213> ORGANISM: Artificial Sequence
<220> FEATURE:
<223> OTHER INFORMATION: BMP4 reverse primer

<400> SEQUENCE: 50
cttccccgtc tcaggtatca                                              20

<210> SEQ ID NO 51
<211> LENGTH: 20
<212> TYPE: DNA
<213> ORGANISM: Artificial Sequence
<220> FEATURE:
<223> OTHER INFORMATION: NOGGIN forward primer

<400> SEQUENCE: 51
tcgaacaccc agaccctatc                                              20

<210> SEQ ID NO 52
<211> LENGTH: 20
<212> TYPE: DNA
<213> ORGANISM: Artificial Sequence
<220> FEATURE:
<223> OTHER INFORMATION: NOGGIN reverse primer

<400> SEQUENCE: 52
tgtaacttcc tccgcagctt                                              20

<210> SEQ ID NO 53
<211> LENGTH: 23
<212> TYPE: DNA
<213> ORGANISM: Artificial Sequence
<220> FEATURE:
<223> OTHER INFORMATION: GAPDH forward primer

<400> SEQUENCE: 53
ccccttcatt gacctcaact aca                                          23

<210> SEQ ID NO 54
<211> LENGTH: 22
<212> TYPE: DNA
<213> ORGANISM: Artificial Sequence
<220> FEATURE:
<223> OTHER INFORMATION: GAPDH reverse primer

<400> SEQUENCE: 54
ttgctgatga tcttgaggct gt                                           22
```

<210> SEQ ID NO 55
<211> LENGTH: 21
<212> TYPE: DNA
<213> ORGANISM: Artificial Sequence
<220> FEATURE:
<223> OTHER INFORMATION: ACTB forward primer

<400> SEQUENCE: 55
cctgaaccct aaggccaacc g                                       21

<210> SEQ ID NO 56
<211> LENGTH: 21
<212> TYPE: DNA
<213> ORGANISM: Artificial Sequence
<220> FEATURE:
<223> OTHER INFORMATION: ACTB reverse primer

<400> SEQUENCE: 56
gctcatagct cttctccagg g                                       21

<210> SEQ ID NO 57
<211> LENGTH: 20
<212> TYPE: DNA
<213> ORGANISM: Artificial Sequence
<220> FEATURE:
<223> OTHER INFORMATION: GAPDH (quantitative) forward primer

<400> SEQUENCE: 57
gtggacctga cctgccgtct                                         20

<210> SEQ ID NO 58
<211> LENGTH: 20
<212> TYPE: DNA
<213> ORGANISM: Artificial Sequence
<220> FEATURE:
<223> OTHER INFORMATION: GAPDH (quantitative) reverse primer

<400> SEQUENCE: 58
ggaggagtgg gtgtcgctgt                                         20

<210> SEQ ID NO 59
<211> LENGTH: 20
<212> TYPE: DNA
<213> ORGANISM: Artificial Sequence
<220> FEATURE:
<223> OTHER INFORMATION: T (quantitative) forward primer

<400> SEQUENCE: 59
aagaaggaaa tgcagcctca                                         20

<210> SEQ ID NO 60
<211> LENGTH: 20
<212> TYPE: DNA
<213> ORGANISM: Artificial Sequence
<220> FEATURE:
<223> OTHER INFORMATION: T (quantitative) reverse primer

<400> SEQUENCE: 60
tactgcaggt gtgagcaagg                                         20

<210> SEQ ID NO 61
<211> LENGTH: 20
<212> TYPE: DNA
<213> ORGANISM: Artificial Sequence
<220> FEATURE:

```
<223> OTHER INFORMATION: CTNNB1 (quantitative) forward primer

<400> SEQUENCE: 61
cccactaatg tccagcgttt                                              20

<210> SEQ ID NO 62
<211> LENGTH: 20
<212> TYPE: DNA
<213> ORGANISM: Artificial Sequence
<220> FEATURE:
<223> OTHER INFORMATION: CTNNB1 (quantitative) reverse primer

<400> SEQUENCE: 62
aacgcatgat agcgtgtctg                                              20

<210> SEQ ID NO 63
<211> LENGTH: 57
<212> TYPE: DNA
<213> ORGANISM: Artificial Sequence
<220> FEATURE:
<223> OTHER INFORMATION: Beta-catenin short hairpin RNA (shRNA) 1

<400> SEQUENCE: 63
ccggaggtgc tatctgtctg ctctactcga gtagagcaga cagatagcac cttttt      57

<210> SEQ ID NO 64
<211> LENGTH: 57
<212> TYPE: DNA
<213> ORGANISM: Artificial Sequence
<220> FEATURE:
<223> OTHER INFORMATION: Beta-catenin short hairpin RNA (shRNA) 2

<400> SEQUENCE: 64
ccgggcttgg aatgagactg ctgatctcga gatcagcagt ctcattccaa gcttttt     57
```